United States Patent
Ahimou et al.

(10) Patent No.: US 12,228,555 B2
(45) Date of Patent: Feb. 18, 2025

(54) SELF-CONTAINED BIOLOGICAL INDICATOR

(71) Applicant: Solventum Intellectual Properties Company, Maplewood, MN (US)

(72) Inventors: Francois Ahimou, Woodbury, MN (US); Kelvin J. Witcher, Hudson, WI (US); Naiyong Jing, Saint Paul, MN (US); Tonya D. Bonilla, Woodbury, MN (US); G. Marco Bommarito, Stillwater, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 1060 days.

(21) Appl. No.: 17/261,084

(22) PCT Filed: Jul. 26, 2019

(86) PCT No.: PCT/US2019/043590
§ 371 (c)(1),
(2) Date: Jan. 18, 2021

(87) PCT Pub. No.: WO2020/023833
PCT Pub. Date: Jan. 30, 2020

(65) Prior Publication Data
US 2021/0311002 A1    Oct. 7, 2021

Related U.S. Application Data

(60) Provisional application No. 62/711,007, filed on Jul. 27, 2018.

(51) Int. Cl.
| | | |
|---|---|---|
| *C12Q 1/22* | (2006.01) | |
| *A61L 2/28* | (2006.01) | |
| *G01N 21/64* | (2006.01) | |
| *G01N 31/22* | (2006.01) | |

(52) U.S. Cl.
CPC .............. *G01N 31/226* (2013.01); *A61L 2/28* (2013.01); *C12Q 1/22* (2013.01); *G01N 21/6428* (2013.01); *G01N 2021/6439* (2013.01)

(58) Field of Classification Search
CPC .... G01N 31/226; G01N 21/6428; C12Q 1/22; A61L 2/28
See application file for complete search history.

(56) References Cited

U.S. PATENT DOCUMENTS

| 5,073,488 A * | 12/1991 | Matner ................. C12Q 1/22 |
| | | 435/31 |
| 8,945,837 B2 * | 2/2015 | Franciskovich ....... C12N 15/74 |
| | | 435/6.1 |
| 8,975,067 B2 | 3/2015 | Foltz |
| 10,047,334 B2 | 8/2018 | Chandrapati |
| 2017/0211035 A1 | 7/2017 | Yirava |

FOREIGN PATENT DOCUMENTS

| CN | 106794271 | 5/2017 |
| CN | 107137741 | 9/2017 |
| EP | 0371682 | 6/1990 |
| JP | 2006-296850 | 11/2006 |

OTHER PUBLICATIONS

International Search Report for PCT International Application No. PCT/US2019/043590, mailed on Feb. 24, 2020, 5 pages.

* cited by examiner

*Primary Examiner* — Randy Boyer
(74) *Attorney, Agent, or Firm* — Mueting Raasch Group

(57) ABSTRACT

The present disclosure is directed to self-contained biological indicators wherein a single type of indicator is capable of being used for various sterilization conditions, including sterilization with steam and/or ethylene oxide. In some embodiments, a single type of biological indicator is capable of being used for different steam sterilization conditions having varied temperatures and sterilization cycles.

7 Claims, 4 Drawing Sheets

SELF-CONTAINED BIOLOGICAL INDICATOR

CROSS REFERENCE TO RELATED APPLICATIONS

This application is a national stage filing under 35 U.S.C. 371 of PCT/US2019/043590, filed Jul. 26, 2019, which claims the benefit of U.S. Provisional Application No. 62/711,007, filed Jul. 27, 2018, the disclosures of which are incorporated by reference in their entirety herein.

The present disclosure is directed to self-contained biological indicators wherein a single type of indicator is capable of being used under various sterilization conditions, including sterilization with steam, ethylene oxide, and/or other sterilants. In some embodiments, a single type of biological indicator is capable of being used under different steam sterilization conditions having varied temperatures and sterilization modalities.

BACKGROUND

The sterilization of equipment, instruments, and other devices is critical in the health care industry. For example, hospitals and other medical institutions frequently sterilize medical instruments and equipment used in treating patients. The particular type of sterilization cycle used to sterilize such equipment can vary based on the particular equipment or devices being sterilized and based on the particular preference of the entity performing the sterilization cycle. However, all such sterilization cycles or processes are typically designed to kill living organisms which might otherwise contaminate the equipment or devices being sterilized.

Various sterilization methods use different cycles or techniques for sterilization. For instance, sterilization may include the administration of steam, dry heat, chemicals (e.g., ethylene oxide), or radiation, to the equipment or devices being sterilized. Steam sterilization is typically efficacious when the equipment being sterilized is heat resistant at high temperatures because the items are exposed to steam having a temperature generally in a range of 121-135° C. The period of exposure to steam depends on the sterilization temperature. For example, for equipment or instruments being sterilized are preferably exposed to the steam sterilization for approximately three minutes at 132° C. However, the exposure period could be up to 30 minutes at 121° C.

Other types of sterilization involve exposing the devices or instruments to chemical agents. A common chemical sterilant used for low-temperature sterilization is ethylene oxide gas. Typically, for ethylene oxide sterilization, the devices being sterilized are exposed to the ethylene oxide gas for a period ranging from one hour at 55° C. to approximately four hours at 38° C. Dry heat sterilization typically involves exposing the devices being sterilized to temperatures in a range of approximately 180° C., or higher, for at least two hours. In many medical applications, the efficacy of the sterilization cycle is critical.

Biological indicators are commonly used to evaluate and validate the effectiveness of a sterilization process in a variety of settings. In general, viable but relatively highly-resistant spores of thermophilic organisms are subjected to the sterilization conditions along with any devices or instruments to be sterilized. In general, the test microorganisms are more resistant to the sterilization cycle than most other organisms that would be present by natural contamination. Applicants have used spores of microorganisms capable of producing an enzyme that catalyzes the reaction of a non-fluorescent substrate to a fluorescent product that can be detected to indicate the presence of surviving spores.

Typically, after completion of the sterilization cycle, the spores are incubated in nutrient medium to determine whether any of the test organisms survived the sterilization procedure. In the conventional biological indicators, growth of a detectable number of organisms can take up to 24 hours for a pH color change indicator.

The biological indicator is then examined to determine whether such growth has taken place. Applicants use rapid readout technology based on a fluorescent response during incubation in the growth medium due to the release of an enzyme during the spore germination and outgrowth. When media comes in contact with viable spores, the spore-associated enzyme interacts with fluorogenic substrate contained in the media. The interaction of the enzyme and substrate results in the cleavage of the substrate to produce a fluorescently-detected compound. An analysis of the fluorescence intensity due to the fluorescent product correlated with other parameters serves to determine whether the sterilization process was successful.

In general, biological indicators are designed for specific cycles and Applicants know of no biological indicator that can be used under all common commercially-available sterilization cycles. The present disclosure is directed to biological indicators that can be used for one or more of the commercial steam sterilization cycles.

SUMMARY

In some embodiments, the present disclosure provides self-contained biological indicators for determining the efficacy of a given sterilization cycle and to items comprising those biological indicators. In other embodiments, the same biological indicator is capable of determining the efficacy of most or all steam sterilization cycles. In some embodiments, the biological indicators can determine the efficacy of a sterilization cycle in less than 60 minutes.

In one aspect, the present disclosure provides a self-contained biological indicator. In some embodiments, the self-contained biological indicator can comprise a housing, bacterial spores comprising, and/or capable of producing, an enzyme capable of catalyzing the cleavage of an enzyme substrate, and a frangible container comprising a liquid composition, wherein the liquid composition comprises the enzyme substrate. The frangible container is adapted to allow the liquid composition to contact the bacterial spores. The cleavage of the enzyme substrate is configured to produce a fluorescently detectable compound. When the liquid composition and the bacterial spores are in contact, the resulting mixture has an initial pH in the range from 7.65 to 8.9.

In some embodiments, the self-contained biological indicator can comprise a housing, a source of biological activity, and an actuatable container. The source comprises and/or capable of producing an enzyme capable of catalyzing the cleavage of an enzyme substrate. The actuatable container comprises a liquid composition. The liquid composition comprises the enzyme substrate and an effective amount of an acidic component and/or a basic component in the source of biological activity and/or the liquid composition so that, when the source of biological activity and the liquid composition are combined, a resulting mixture of the source of biological activity and the liquid composition has an initial pH in the range from 7.65 to 8.9. The actuatable container can be actuated to allow the liquid composition to contact the bacterial spores. A product of the cleavage of the enzyme substrate by the enzyme is a fluorescently detectable compound. The source of biological activity and/or the liquid composition comprises an effective amount of an acidic component and/or a basic component such that, when the source of biological activity and the liquid composition are combined, a resulting mixture of the source of biological activity and the liquid composition has an initial pH in the range from 7.65 to 8.9

Optionally, in any of the above embodiments, the self-contained biological indicator is inside a process-challenge device. In any of the above embodiments of the self-contained biological indicator, the pH range is preferably 7.8 to 8.4.

In another aspect, the present disclosure provides a kit. In some embodiments, the kit can comprise a source of biological activity comprising and/or capable of producing an enzyme capable of catalyzing the cleavage of an enzyme substrate; the enzyme substrate; a liquid composition comprising the enzyme substrate; and an effective amount of an acidic component and/or a basic component such that, when the source of biological activity and the liquid composition are combined, a resulting mixture of the source of biological activity and the liquid composition has an initial pH in the range from 7.65 to 8.9. A product of the cleavage of the enzyme substrate by the enzyme can be detected by its fluorescence. In some embodiments, the kit can comprise any of the above embodiments of the self-contained biological indicator.

In any of the above embodiments of the kit, the liquid medium can comprise a component selected from the group consisting of the enzyme substrate, the acidic component, the basic component, or a combination of any two or more of the foregoing components. In any of the above embodiments of the kit, the source of biological activity can comprise an isolated enzyme or a plurality of bacterial spores. In yet another aspect, the present disclosure provides a system for use in determining the efficacy of a sterilization process. The system can comprise any of the above embodiments of the self-contained biological indicator, and an automated reader. The automated reader can be configured to receive at least a portion of the biological indicator, direct a first wavelength of electromagnetic radiation into the liquid composition in the housing, and detect or measure a quantity of a second wavelength of electromagnetic radiation emitted by the fluorescent product. In any of the above embodiments of the system, the self-contained biological indicator is adapted to be used to determine efficacy of any steam sterilization process selected from the group consisting of 121 C gravity process, 121 C pre-vac process, 121 C SFPP process, 132° C. gravity process, 132 C pre-vac process, 132 C SFPP process, 134 C pre-vac process, 134 C SFPP process, 135 C gravity process, 135 C pre-vac process, and 135 C SFPP process.

In yet another aspect, the present disclosure provides a method for determining efficacy of a sterilization process. The method can comprise exposing a source of biological activity to the sterilization process, wherein the source of biological activity comprises and/or is capable of producing an enzyme capable of reacting with a fluorogenic enzyme substrate to produce a fluorescent product. After exposing the source to the sterilization process, bringing the source into contact with a liquid composition, incubating the mixture for a period of time, and detecting the fluorescent product formed in the mixture. Bringing the source into contact with the liquid composition comprises placing the source in liquid contact with the fluorogenic enzyme substrate. After bringing the source into contact with the liquid composition, a resulting mixture of the source of biological activity and the liquid composition has an initial pH in the range from 7.65 to 8.9.

In any of the above embodiments of the method, incubating the mixture for a period of time comprises incubating the mixture at a specified temperature. The specified temperature is any temperature suitable for detecting growth of the test microorganism and/or for facilitating the reaction catalyzed by the enzyme present in or produced by the source of biological activity (e.g. a test microorganism). In some embodiments, the specified temperature is about 37° C. to about 60° C.

In any of the above embodiments of the method, incubating the mixture for a period of time comprises incubating the mixture at a specified temperature. In any of the above embodiments of the method, the period of time is a specified period of time, wherein the specified period of time is less than or equal to 180 minutes, wherein detecting less than a threshold quantity of the fluorescent product after the specified period of time indicates efficacy of the sterilization process. In any of the above embodiments of the method, detecting the fluorescent product can comprise quantifying fluorescence emitted by the fluorescent product.

The self-contained biological indicators of any of the above embodiments are capable of determining the efficacy of one or more sterilization cycles chosen from the powerset of the following eleven cycles: 121° C. gravity, 121° C. pre-vac, 121° C. SFPP, 132° C. gravity, 132° C. pre-vac, 132° C. SFPP, 134° C. pre-vac, 134° C. SFPP, 135° C. gravity, 135° C. pre-vac, and 135° C. SFPP, preferably within less than 1 hr. See definitions of "powerset" and each of the sterilization cycles in the sections below. The inventors have envisioned all subsets from every possible combination of the above cycles, whether being a single cycle of more than one cycle, as being part of the chosen set of cycles in which a single biological indicator can be used.

All scientific and technical terms used herein have meanings commonly used in the art unless otherwise specified. The definitions provided herein are to facilitate understanding of certain terms used frequently in this application and are not meant to exclude a reasonable interpretation of those terms in the context of the present disclosure.

Unless otherwise indicated, all numbers in the description and the claims expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

The recitation of numerical ranges by endpoints includes all numbers subsumed within that range (e.g. a range from 1 to 5 includes, for instance, 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

The term "powerset" as used herein for a given set S having n elements refers to the mathematical definition of a powerset and all possible subsets of S, without including the empty set, but including S itself, having from 1 to n elements in every combination and is denoted as P(S). Applicants note that the mathematical definition of a powerset includes the empty set (a set having no elements. However, the definition adopted here by Applicants excludes the empty set and includes all subsets having at least one element, including the full set of n elements (S). In general, the powerset includes all subsets having "i" elements for i=1 to n−1, and the subset having all n elements (n). For instance, the powerset of a subset S having the elements a, b, and c (n=3) includes the following 7 subsets: all possible subsets having one element: {(a), (b), (c)}; all possible subsets having any possible combination two elements: {(a, b), (a, c), (b, c)}, and the subset having all 3 elements: (a, b, c).

The term "actuatable container", as used herein, refers to a container that can be actuated, when desired, to release contents therein. The container can be actuated, for example, the container can by dislodging or removing a plug, by actuating a valve to change it from a "closed" state to an "open" state, or by otherwise breaching at least a portion of the container.

The term "frangible container" refers to any container that can be acted upon to release its contents, for example by breaking it, puncturing it, shattering it, cutting it, etc.

The term "process challenge device," abbreviated as "PCD," refers to a container that may comprise a biological indicator inside and which contains an additional barrier to a sterilant to reach its contents (e.g., a biological indicator) compared to the path the sterilant would need to travel to reach the items insider the PCD (e.g., biological indicator) if the items were not inside the PCD. A PCD is also known as a "test pack" and both terms are being used interchangeably in this disclosure. A PCD is designed to simulate sterilization conditions used for instruments or other items to be sterilized and generally comprise a defined challenge to the sterilization process. In its most simply embodiment, a PCD is a sealed container that has an inlet (e.g., an orifice or puncture) for a sterilant to be able to reach the interior of the container.

The term "fluorescently detectable compound" refers to a compound that is susceptible to detection by fluorescence, even if the compound may not be fluorescent at all times and only fluoresces when exited by energy of the proper wavelength. Examples of fluorescently detectable compound useful in this patent application include the products of an enzymatic reaction of a substrate with a cleaving enzyme where the substrate is not fluorescently detectable using the excitation wavelengths used to detect the enzymatic reaction product. The fluorescent detection can be carried out in solution or on a substrate. An example of such a compound is 4-methylumbelliferone (4-MU), which is the product of the enzymatic cleavage of 4-methylumbelliferyl-α-D-glucopyranoside by the enzyme α D glucosidase.

The term "adjacent" refers to the relative position of two elements, such as, for example, two layers, that are close to each other and may or may not be necessarily in contact with each other or that may have one or more layers separating the two elements as understood by the context in which "adjacent" appears.

The term "immediately adjacent" refers to the relative position of two elements, such as, for example, two layers, that are next to each other and in contact with each other and have no intermediate layers separating the two elements. The term "immediately adjacent," however, encompasses situations where one or both elements (e.g., layers) have been treated with a primer, or whose surface has been modified to affect the properties thereof, such as etching, embossing, etc., or has been modified by surface treatments, such as corona or plasma treatment, etc. that may improve adhesion.

"Time to result", and its acronym "TTR", and "Time to Turn" as used herein, refers to the shortest period of time required to detect a fluorescent signal generated by sources of biological activity (e.g., enzyme, test microorganism or spore) that remain active after exposure to a sterilization process. Typically, the TTR is determined by using an automated reader to detect the fluorescent signal.

The above summary is merely intended to provide a cursory overview of the subject matter of the present disclosure and is not intended to describe each disclosed embodiment or every implementation of the present invention. The description that follows more particularly exemplifies illustrative embodiments. In several places throughout the application, guidance is provided through lists of examples, which can be used in various combinations. In each instance, the recited list serves only as a representative group and should not be interpreted as an exclusive list.

DETAILED DESCRIPTION

Figure 1:
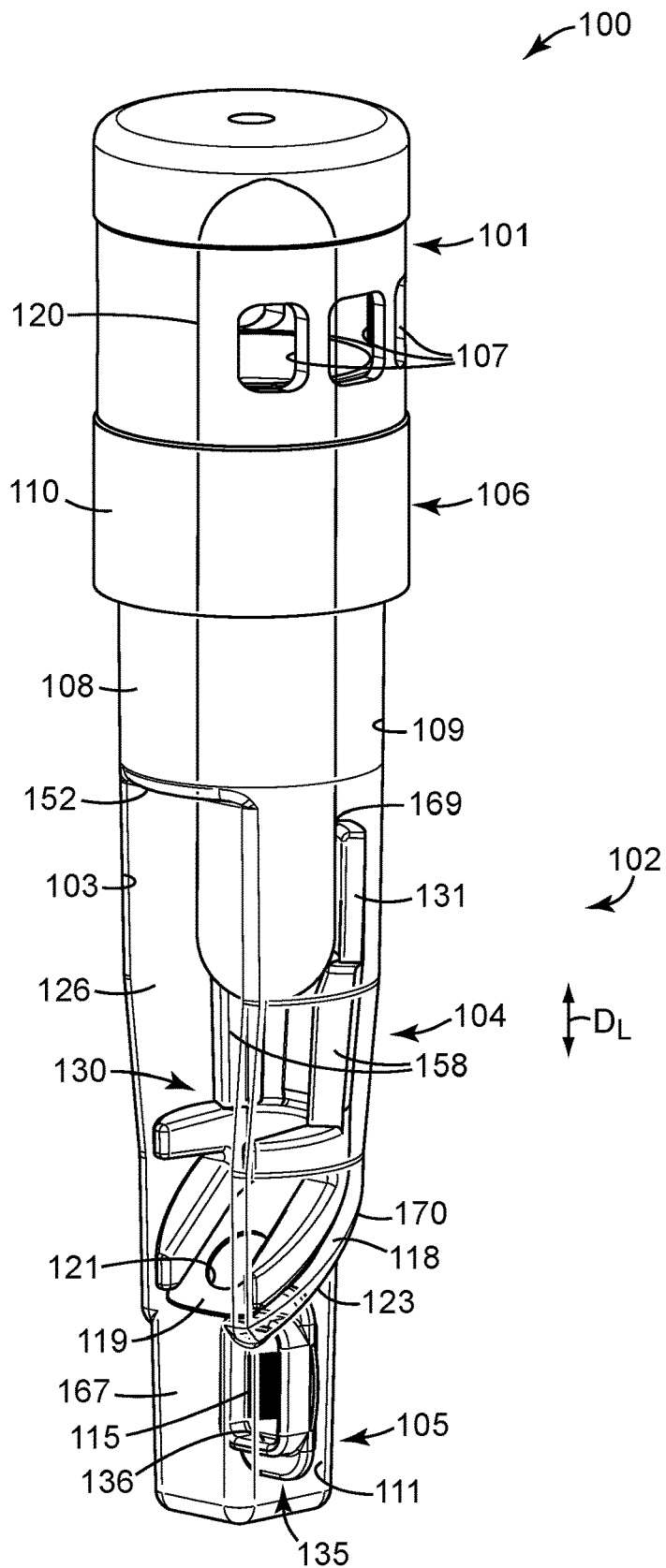
FIG. 1 represents a schematic view of an exemplary biological indicator of the present disclosure.

In some embodiments, the present disclosure is directed to self-contained biological indicators comprising:
a housing,
bacterial spores comprising, and/or capable of producing, an enzyme capable of catalyzing the cleavage of an enzyme substrate chosen from,
a frangible container comprising a liquid composition, wherein the liquid composition comprises: the enzyme substrate,
wherein the frangible container is adapted to allow the liquid composition to contact the bacterial spores;
wherein the cleavage of the enzyme substrate is configured to produce a fluorescently detectable compound, wherein, when the liquid composition and the bacterial spores are in contact which may occur by, for example, mixing, the resulting mixture has an initial pH in the range from 7.65 to 8.9, while in some embodiments, the range is preferably 7.8 to 8.4.

Optionally, in some embodiments, the self-contained biological indicator is inside a process-challenge device.

In some embodiments, the present disclosure is directed to self-contained biological indicators comprising:
  a housing;
  a source of biological activity, the source comprising and/or capable of producing an enzyme capable of catalyzing the cleavage of an enzyme substrate;
  an actuatable container comprising a liquid composition, wherein the liquid composition comprises the enzyme substrate; and
  an effective amount of an acidic component and/or a basic component in the source of biological activity and/or the liquid composition so that, when the source of biological activity and the liquid composition are combined, a resulting mixture of the source of biological activity and the liquid composition has an initial pH in the range from 7.65 to 8.9;
  wherein the actuatable container is adapted to allow the liquid composition to contact the source of biological activity;
  wherein a product of the cleavage of the enzyme substrate by the enzyme is a fluorescently detectable compound.

Optionally, in some embodiments, the self-contained biological indicator is disposed inside a process-challenge device.

In addition, the present disclosure provides systems and methods for determining efficacy of a sterilization process.

Housing

In general, the housing refers to a container, usually an outer container, having walls impermeable to a sterilant, where other components of the biological indicator are located. The housing may be inside a process challenge device or may be a process challenge device itself. In some embodiments, the housing may have dimensions useful to produce a flat or generally planar biological indicator. This disclosure encompasses housings of any shape and dimensions.

The housing contains at least one opening that allows flow of a sterilant to the interior of the housing (sterilant pathway). In some embodiments, the housing may comprise a body with an opening and a cap to close that opening. In some embodiments, the cap may be capable of completely sealing the housing and eliminating any fluid communication between the interior of the housing and ambiance (e.g., closing the sterilant pathway). In general, the cap has an open position in which there is an opening (e.g., a gap) between the cap and the body of the container that allows flow of liquid or gas (e.g., a sterilant) into and out of the interior of the housing. The cap also has a closed position where the opening is sealed and any fluid flow through the gap is eliminated. In other embodiments, the cap may comprise vents that allow passage of a sterilant to the interior of the housing and create an additional sterilant pathway, even if the cap is present and in the closed position. In other preferred embodiments, however, when the cap comprises vents, placing the cap in the closed position simultaneously closes: (a) the gap between the cap and the body of the container and (b) the vents present on the cap, essentially closing the sterilant pathway.

In other embodiments, the cap may lack vents and the only sterilant pathway may be through the space between the cap and the body of the housing (or through another opening or vent, if present on the body) when the cap is the open position. In some embodiments, if vents exist on the housing, they are located on the cap. In embodiments where no other opening exists besides the opening between the cap and the body of the housing, then placing the cap in the closed position completely seals off the interior of the housing, which stops the fluid communication between the interior of the housing and ambience. In those embodiments, the sterilant pathway may be sealed when the cap is in the closed position.

Source of Biological Activity

Articles of the present disclosure comprise a source of biological activity. In certain embodiments, the source of biological activity may be a plurality of test microorganisms. In certain embodiments, the source of biological activity may be a plurality of spores. Alternatively, or additionally, the source of biological activity may be a source of active enzyme.

The source of active enzyme may be: 1) the purified or isolated enzyme derived from an appropriate microorganism; 2) a microorganism to which the enzyme is indigenous or added by genetic engineering; or 3) a microorganism to which the enzyme has been added during sporulation or growth, such that the enzyme is incorporated or associated with the microorganism, e.g., an enzyme added to a spore during sporulation which becomes incorporated within the spore. Preferred microorganisms which may be utilized as the source of an enzyme useful in the practice of the present invention are bacteria or fungi in either the spore or vegetative state. Particularly preferred sources of enzyme include, without limitation, *Bacillus, Clostridium, Neurospora,* and *Candida* species of microorganisms.

When a microorganism is used as the source of active enzyme, the method of the present invention may include the step of incubating any of the microorganisms which remain viable, following the completion of the sterilization cycle, with an aqueous nutrient medium. Inclusion of this step confirms by conventional techniques whether the sterilization conditions had been sufficient to kill all of the microorganisms in the indicator, indicating that the sterilization conditions had been sufficient to sterilize all of the items in the sterilizer. If growth of the microorganism is used in a conventional manner to confirm the results of the enzyme test, the microorganism should be one which is conventionally used to monitor sterilization conditions. These conventionally used microorganisms are generally many times more resistant to the sterilization process being employed than most organisms encountered in natural contamination. The bacterial spore is recognized as the most resistant form of microbial life. It is the life form of choice in all tests for determining the sterilizing efficacy of devices, chemicals and processes. Spores from *Bacillus* and Clostridia species are the most commonly used to monitor sterilization processes utilizing saturated steam, dry heat, gamma irradiation and ethylene oxide.

Alternatively, in the event that isolated enzyme is utilized, or the microorganism used as the source of the enzyme is not more resistant to the sterilization conditions than the natural contaminants, another microorganism commonly used to monitor sterilization conditions can be exposed to the sterilization cycle along with the enzyme source. Again, in such a case, the method of the present invention may include the step of incubating any viable microorganism remaining after the sterilization cycle with an aqueous nutrient medium to confirm the sterilization efficacy.

Test Microorganisms (e.g., Spores)

Generally, test microorganisms are chosen to be used in a biological indicator that are particularly resistant to a given sterilization process. In certain embodiments, the biological indicators of the present disclosure include a viable culture of a known species of microorganism, usually in the form of microbial spores. Spores (e.g., bacterial spores), rather than the vegetative form of the microorganisms, are used at least partly because vegetative microorganisms are known to be relatively easily killed by sterilizing processes. Additionally, spores also have superior storage characteristics and could remain in their dormant state for years. As a result, sterilization of an inoculum of a standardized spore strain provides a higher degree of confidence that inactivation of all microorganisms in a sterilizing chamber has occurred.

By way of example only, the present disclosure describes the microorganisms used in the biological indicator as being "spores;" however, it should be understood that the type of microorganism (e.g., spore) used in a particular embodiment of the biological indicator is selected for being resistant to the particular sterilization process contemplated (more resistant than the microorganisms normally present on the items to be sterilized so that inactivation of the test microorganisms indicates a successful sterilization.). Accordingly, different embodiments of the present disclosure using different sterilants may use different microorganisms, depending on the sterilization process for which the particular embodiment is intended.

In general, the spores used in a particular system are selected according to the sterilization process at hand. For example, for a steam sterilization process, *Geobacillus stearothermophilus* or *Bacillus stearothermophilus* can be used. In another example, for an ethylene oxide sterilization process, *Bacillus atrophaeus* (formerly *Bacillus subtilis*) can be used. In some embodiments, the spores can include, but are not limited to, at least one of *Geobacillus stearothermophilus*, *Bacillus stearothermophilus*, *Bacillus subtilis*, *Bacillus atrophaeus*, *Bacillus megaterium*, *Bacillus coagulans*, *Clostridium sporogenes*, *Bacillus pumilus*, or combinations thereof.

Enzymes and Enzyme Substrates

The bacterial spores either comprise an enzyme capable of catalyzing the cleavage of an enzyme substrate to produce a fluorescently detectable compound, or are capable of producing such an enzyme, or both. The enzymes useful in biological indicators of the present disclosure include extracellular and intracellular enzymes whose activity correlates with the viability of at least one of the microorganisms commonly used to monitor sterilization efficacy ("test" microorganism or "test spores"). In this context, "correlates" means that the enzyme activity, over background, can be used to predict growth of the test microorganism. The enzyme should be one which, following a sterilization cycle which is sublethal to the test microorganism, remains sufficiently active to react with a substrate for the enzyme, within twenty-four hours, and in preferred embodiment within eight hours or less, yet be inactivated or appreciably reduced in activity following a sterilization cycle which would be lethal to the test microorganism.

Examples of suitable enzymes include α-glucosidase, α-galactosidase, lipase, esterase, acid phosphatase, alkaline phosphatase, proteases, aminopeptidase, chymotrypsin, β-glucosidase, galactosidase, α-glucoronidase, β-glucoronidase, phosphohydrolase, plasmin, thrombin, trypsin, calpain, α-mannosidase, β-mannosidase, a-L-fucosidase, leucine aminopeptidase, a-L-arabinofuranosidase, cysteine aminopeptidase, valine aminopeptidase, β-xylosidase, α-L-iduronidase, glucanase, cellobiosidase, cellulase, α-arabinosidase, glycanase, sulfatase, butyrate, glycosidase, arabinoside, and a combination of any two or more of the foregoing enzymes. In certain embodiments of the articles, kits, systems and methods of the present disclosure, the source of biological activity used therein comprises an isolated or otherwise purified form of any of the foregoing suitable enzymes.

In the context of this application, an enzyme substrate comprises a substance or mixture of substances that, when acted upon by an enzyme, are converted into an enzyme-modified product. Although the preferred substrate produces a fluorescently detectable compound, in other embodiments, the product of the enzymatic action may be a luminescent or colored material. In other embodiments, however, the enzyme substrate can consist of a compound which when reacted with the enzyme, will yield a product that will react with an additional compound or composition to yield a luminescent, fluorescent, or colored material. Preferably, if the substrate is to be included in the indicator device during sterilization, the substrate should not spontaneously break down or convert to a detectable product during sterilization or incubation. For example, in devices used to monitor steam and dry heat sterilization, the substrate must be stable at temperatures between about 20° C. and 180° C. Preferably also, where the enzyme substrate is to be included with conventional growth media, it must be stable in the growth media, e.g., not auto fluoresce in the growth media.

In general, there are two basic types of enzyme substrate that can be used in the biological indicators of this disclosure. The first type of substrate can be either fluorogenic (or chromogenic), and can be given a chemical formula such as, AB. When acted upon by the enzyme, AB breaks down into the products A and B. B, for example, could be either fluorescent or colored. A specific example of a fluorogenic substrate of this type are salts of 4-methylumbelliferyl. Other fluorogenic substrates of this type include the derivatives of 4-methylumbelliferyl, 7-amido-4-methylcoumarin (7-AMC), indoxyl and fluorescein. An example of a chromogenic substrate of this type is 5-bromo-4-chloro-3-indolyl phosphate. In the presence of phosphatase, the substrate will be broken down into indigo blue and phosphate. Other chromogenic substrates of this type include derivatives of 5-bromo-4-chloro-3-indolyl, nitrophenol and phenolphthalein, listed below.

The second type of substrate can be given the chemical formula CD, for example, which will be converted by a specific enzyme into C and D. In this case, however, neither C nor D will be fluorescent or colored, but either C or D is capable of being further reacted with compound Z to give a fluorescent or colored compound, thus indicating enzyme activity. A specific fluorogenic example of this type is the amino acid lysine. In the presence of the enzyme lysine decarboxylase, lysine loses a molecule of $CO_2$. The remaining part of the lysine is then called cadaverine, which is strongly basic. A basic indicator such as 4-methylumbelliferone can be incorporated and will fluoresce in the presence of a strong base. A chromogenic substrate of this type would be 2-naphthyl phosphate. The enzyme phosphatase reacts with the substrate to yield beta-naphthol. The liberated beta-naphthol reacts with a chromogenic reagent containing 1-diazo-4-benzoylamino-2, 5-diethoxybenzene, commercially available as "Fast Blue BB Salt" from Sigma Chemical, to produce a violet color.

As mentioned above, a preferred enzyme substrate in some embodiments is a fluorogenic substrate, defined herein as a compound capable of being enzymatically modified, e.g., by hydrolysis or other enzymatic action, to give a derivative fluorophore that has a measurably modified or increased fluorescence.

A skill in the art would understand that suitable fluorogenic compounds are in themselves either non-fluorescent or meta-fluorescent (i.e., fluorescent in a distinctly different way e.g., either by color or intensity, compared to the corresponding enzyme-modified products). In that regard, appropriate wavelengths of excitation and detection, in a manner known to users of fluorometric techniques, are used to separate the fluorescence signal developed by the enzyme modification from any other fluorescence that may be present.

Non-limiting examples of suitable enzymatic substrates can include, for example, derivatives of coumarin including 7-hydroxycoumarin (also known as umbelliferone or 7-hydroxy-2H-chromen-2-one) derivatives and 4-methylumbelliferone (7-hydroxy-4-methylcoumarin) derivatives including: 4-methylumbelliferyl alpha-D-glucopyranoside, 4-methylumbelliferyl alpha-D-galactopyranoside, 4-methylumbelliferyl heptanoate, 4-methylumbelliferyl palmitate, 4-methylumbelliferyl oleate, 4-methylumbelliferyl acetate, 4-methylumbelliferylnonanoate, 4-methylumbelliferyl caprylate, 4-methylumbelliferyl butyrate, 4-methylumbelliferyl-beta-D-cellobioside, 4-methylumbelliferyl acetate, 4-methylumbelliferyl phosphate, 4-methylumbelliferyl sulfate, 4-methylumbelliferyl-beta-trimethylammonium cinnamate chloride, 4-methylumbelliferyl-beta-D-N, N',N"-triacetylchitotriose, 4-methylumbelliferyl-beta-D-xyloside, 4-methylumbelliferyl-N-acetyl-beta-D-glucosaminide, 4-methylumbelliferyl-N-acetyl-alpha-D-glucosaminide, 4-methylumbelliferyl propionate, 4-methylumbelliferyl stearate, 4-methylumbelliferyl-alpha-L-arabinofuranoside, 4-methylumbelliferyl alpha-L-arabinoside; methyl umbelliferyl-beta-D-N,N'-diacetyl chitobioside, 4-methylumbelliferyl elaidate, 4-Methylumbelliferyl-alpha-D-mannopyranoside, 4-methylumbelliferyl-beta-D-mannopyranoside, 4-methylumbelliferyl-beta-D-fucoside, 4-methylumbelliferyl-alpha-L-fucoside, 4-methylumbelliferyl-beta-L-fucoside, 4-methylumbelliferyl-alpha-D-galactoside, 4-me thy-lumbelliferyl-beta-D-galactoside, 4-trifluoromethylumbelliferyl beta-D-galactoside, 4-methylumbelliferyl-alpha-D-glucoside, 4-methylumbelliferyl-beta-D-glucoside, 4-methylumbelliferyl-7,6-sulfo-2-acetamido-2-deoxy-beta-D-glucoside, 4-methylumbelliferyl-beta-D-glucuronide, 6,8-difluor-4-methylumbelliferyl-beta-D-glucuronide, 6,8-difluoro-4-methylumbelliferyl-beta-D-galactoside, 6,8-difluoro-4-methylumbelliferyl phosphate, 6,8-difluoro-4-methylumbelliferyl beta-D-xylobioside, for example. The second substrate can also be derivatives of 7-amido-4-methylcoumarin, including: Ala-Ala-Phe-7-amido-4-methylcoumarin, Boc-Gln-Ala-Arg-7-amido-4-methylcoumarin hydrochloride, Boc-Leu-Ser-Thr-Arg-7-amido-4-methylcoumarin, Boc-Val-Pro-Arg-7-amido-4-methylcoumarin hydrochloride, D-Ala-Leu-Lys-7-amido-4-methylcoumarin, L-Alanine 7-amido-4-methylcoumarin trifluoroacetate salt, L-Methionine 7-amido-4-methylcoumarin trifluoroacetate salt, L-Tyrosine 7-amido-4-methylcoumarin, Lys-Ala-7-amido-4-methylcoumarin dihydrochloride, N-p-Tosyl-Gly-Pro-Arg 7-amido-4-methylcoumarin hydrochloride, N-Succinyl-Ala-Ala-Phe-7-amido-4-methylcoumarin, N-Succinyl-Ala-Ala-Pro-Phe-7-amido-4-methylcoumarin, N-Succinyl-Ala-Phe-Lys 7-amido-4-methylcoumarin acetate salt, N-Succinyl-Leu-Leu-Val-Tyr-7-Amido-4-methylcoumarin, D-Val-Leu-Lys 7-amido-4-methylcoumarin, Fmoc-L-glutamic acid 1-(7-amido-4-methylcoumarin), Gly-Pro-7-amido-4-methylcoumarin hydrobromide, L-Leucine-7-amido-4-methylcoumarin hydrochloride, L-Proline-7-amido-4-methylcoumarin hydrobromide; other 7-hydroxycoumarin derivatives including 3-cyano-7-hydroxycoumarin (3-cyanoumbelliferone), and 7-hydroxycoumarin-3-carboxylic acid esters such as ethyl-7-hydroxycoumarin-3-carboxylate, methyl-7-hydroxycoumarin-3-carboxylate, 3-cyano-4-methylumbelliferone, 3-(4-imidazolyl)umbelliferone; derivatives of fluorescein including: 2',7'-Bis-(2-carboxyethyl)-5- (and -6-) carboxyfluorescein, 2',7'-bis-(2-carboxypropyl)-5- (and -6-)-carboxyfluorescein, 5- (and 6)-carboxynaphthofluorescein, Anthofluorescein, 2',7'-Dichlorofluorescein diacetate, 5(6)-Carboxyfluorescein, 5(6)-Carboxyfluorescein diacetate, 5-(Bromomethyl)fluorescein, 5-(Iodoacetamido)fluorescein, 5-([4,6-Dichlorotriazin-2-yl]amino)fluorescein hydrochloride, 6-Carboxyfluorescein, Eosin Y, Fluorescein diacetate 5-maleimide, Fluorescein-O'-acetic acid, O'-(Carboxymethyl)fluoresceinamide, anthofluorescein, rhodols, halogenated fluorescein; derivatives of rhodamine including: Tetramethylrhodamine, Carboxy tetramethyl-rhodamine, Carboxy-X-rhodamine, Sulforhodamine 101 and Rhodamine B; afluorescamine derivatives; derivatives of benzo-xanthene dyes including: seminaphthofluorones, carboxy-seminaphthofluorones seminaphthofluoresceins, seminaphthorhodafluors; derivatives of cyanine including sulfonated pentamethine and septamethine cyanine.

In some embodiments, the enzyme whose activity is to be detected may be chosen from alpha-D-glucosidase, chymotrypsin, or fatty acid esterase. In the case of *Bacillus stearothermophilus*, the fluorogenic enzyme substrate is preferably 4-methylumbelliferyl-alpha-D-glucoside, 7-glutarylphenylalanine-7-amido-4-methyl coumarin, or 4-methylumbelliferyl heptanoate. If the enzyme whose activity is to be detected is alpha-L-arabinofuranosidase, e.g., derived from *Bacillus atrophaeus*, a preferred fluorogenic enzyme substrate is 4-methylumbelliferyl-alpha-L-arabinofuranoside. In preferred embodiments, 4-methylumbelliferyl alpha-D-glucopyranoside is the enzyme substrate used to produce the metabolic activity and the enzyme is a glucosidase, such as beta-D-glucosidase.

Sterilization Processes

Biological indicators of the present disclosure may be used to monitor the effectiveness of one or more types of sterilization procedures, including sterilization procedures that use various sterilants, such as steam (e.g., pressurized steam), vapor phase hydrogen peroxide (which may or may not include hydrogen peroxide plasma), ethylene oxide gas, dry heat, propylene oxide gas, methyl bromide, chlorine dioxide, formaldehyde and peracetic acid (alone or with a vapor phase of another material), ozone, radiation, and combinations thereof.

In at least some of the sterilization processes, an elevated temperature, for example, 50° C., 60° C., 100° C., 121° C., 132° C., 134° C., 135° C. or the like, is included or may be encountered in the process. In addition, elevated pressures and/or a vacuum may be encountered, for example, 15 psi ($1 \times 10^5$ Pa) at different stages within a single given sterilization cycle, or in different sterilization cycles.

In the case of steam being the sterilant, the sterilization temperatures can include 121° C., 132° C., 134° C., 135° C. The instant biological indicators are suitable for steam sterilization cycles at each of the temperatures above and for each temperature the cycle can have a different air removal process chosen from gravity, prevacuum ("pre-vac"), and steam flush pressure pulse (SFPP). Each of these cycles may have different exposure times depending on the type of instruments/devices being sterilized. In this disclosure, pre-vacuum and SFPP are also labeled as Dynamic Air Removal (DAR) cycles.

A tabular representation of exemplary steam sterilization cycles in which the present biological indicators can be used is shown below:

| 121° C. | | | 132° C. | | | 134° C. | | | 135° C. | | |
|---|---|---|---|---|---|---|---|---|---|---|---|
| Gravity | Pre-Vac | SFPP | Gravity | Pre-Vac | SFPP | Gravity | Pre-Vac | SFPP | Gravity | Pre-Vac | SFPP |

In this disclosure, the term a "T gravity" sterilization cycle refers to a steam process where the sterilization temperature is T° C. and where air is removed (conditioning) from the sterilization chamber as a result of steam displacement. In this case, the force of gravity causes the heavier gas (air) to exit the chamber via the sterilizer drain as steam enters the chamber. In general, gravity cycles require more exposure time because the air removal method is more passive in nature. For instance, a "121 gravity" cycle is a steam sterilization carried out at 121° C. under gravity conditioning.

A "T pre-vac" sterilization cycle refers to a steam process where the sterilization temperature is T° C. and where air removal is done by mechanical vacuum evacuation in conjunction with steam injections. As a consequence of this conditioning method, the pressure in the sterilization chamber can decrease below atmospheric values during the evacuation cycle and can increase to positive pressures when steam is being introduced. For instance, "121 pre-vac" sterilization cycle refers to a steam process where the sterilization temperature is 121° C. and the conditioning occurs via vacuum evacuations.

A "T SFPP" sterilization cycle refers to a steam process where the sterilization temperature is PC and where conditioning is carried out through a series of pressurizations and flushes with steam. During a SFPP process, the pressure in the chamber does not drop below atmospheric (no vacuum is drawn). For example, a "121 SFPP cycle refers to a steam process where the sterilization temperature is 121° C. and the conditioning occurs via steam flush pressure pulses.

In this disclosure, a "dynamic air removal" cycle refers to a sterilization cycle that uses either prevacuum or SFPP conditioning.

In other embodiments, the biological indicators of the present disclosure may be used to monitor the effectiveness of a vapor phase sterilization procedure that uses an oxidizing sterilant. In some embodiments, the biological indicators may be used to monitor the effectiveness of any of the hydrogen peroxide sterilization procedures known in the art. More preferably, the biological indicator may be used to monitor the effectiveness of a hydrogen peroxide vapor phase sterilization procedure.

While aqueous hydrogen peroxide ($H_2O_2$) has a long history of use as a sterilant, the concept of vapor-phase hydrogen peroxide (VPHP) sterilization has been developed within the past decade. This process is a low temperature sterilization process that kills a wide range of microorganisms including bacterial endospore-forming bacteria commonly used as challenge organisms to evaluate and validate the effectiveness of sterilization cycles in hospitals. A major advantage of hydrogen peroxide is its short exposure cycle time (few minutes). Furthermore, at the end of a hydrogen peroxide sterilization process, only air and water remain in the chamber. Significantly, the novel features of the biological indicators described herein allow for the development of a rapid-readout hydrogen peroxide biological indicator.

In general, a sterilization process includes placing the biological indicator of the present disclosure in a sterilizer. In some embodiments, the sterilizer includes a sterilization chamber that can be sized to accommodate a plurality of articles to be sterilized and can be equipped with a means of evacuating air and/or other gases from the chamber and a means for adding a sterilant to the chamber. The self-contained biological indicator can be positioned in areas of the sterilizer that are most difficult to sterilize. Alternately, the biological indicator can be positioned in process challenge devices to simulate sterilization conditions where sterilant may not be delivered as directly as would be the case in more favorable sterilization circumstances.

The sterilant can be added to the sterilization chamber after evacuating the chamber of at least a portion of any air or other gas present in the chamber. Alternatively, sterilant can be added to the chamber without evacuating the chamber. A series of evacuation steps can be used to assure that the sterilant reaches all desired areas within the chamber and contacts all desired article(s) to be sterilized, including the biological indicator.

The self-contained biological indicators are capable of determining the efficacy of one or more steam sterilization cycles chosen from the powerset of the following eleven cycles: 121 C gravity, 121 C pre-vac, 121 C SFPP, 132 C gravity, 132 C pre-vac, 132 C SFPP, 134 C pre-vac, 134 C SFPP, 135 C gravity, 135 C pre-vac, and 135 C SFPP, preferably within less than 1 hr.

pH-Affecting Components

In some embodiments, a self-contained biological indicator of the present disclosure comprises an effective first amount of an acidic component and/or an effective second amount of a basic component disposed in the housing. The first and/or second amounts, when present in the housing are effective such that, when the source of biological activity (e.g., test microorganisms, spores, or an enzyme activity) and the liquid composition described herein are combined (e.g., in the housing), a resulting mixture of the source of biological activity and the liquid composition has an initial pH in the range from 7.65 to 8.9.

The initial pH of the resulting mixture may be affected by one or more components in the biological sterilization indicator including, for example, the source of biological activity and one or more nutrients or other compounds disposed (e.g., in the liquid composition and/or in a dry form) in the housing.

The acidic component comprises one or more acidic compounds that do not substantially inhibit the growth, germination, or detection of spores and/or test microorganisms in the resulting mixture. Alternatively, or additionally, the acidic component comprises one or more acidic compounds that do not substantially inhibit the detection of the source of biological activity (e.g., an enzyme activity) in the resulting mixture.

The basic component comprises one or more basic compounds that do not substantially inhibit the growth, germination, or detection of spores and/or test microorganisms in the resulting mixture. Alternatively, or additionally, the basic component comprises one or more basic compounds that do not substantially inhibit the detection of the source of biological activity (e.g., an enzyme activity) in the resulting mixture.

The acidic component and/or basic component may be present in the housing in the liquid composition. Alternatively, or additionally, the acidic component and/or basic component may be present in the housing mixed, and optionally dried, with the source of biological activity (e.g., the test microorganism, spores, or enzyme activity). In some embodiments, the acidic component and/or basic component may comprise a buffering agent. In some embodiments, the buffering agent can be disposed in the liquid composition. In some embodiments, the buffering agent can be disposed in the housing separated from the liquid composition. In some embodiments, the buffering agent can be disposed in a dry form separated from or mixed with the source of biological activity (e.g., test microorganisms, spores, and/or enzyme activity). In some embodiments, the buffering agent can be disposed in the liquid composition and be disposed in the housing separated from the liquid composition.

Liquid Composition

The liquid composition is located in the actuatable (e.g., frangible) container and contains one or more of the enzyme substrates mentioned above. In certain embodiments, the enzyme substrate is 4-methylumbelliferyl-alpha-D-glucoside (MUG). In some embodiments, the liquid composition may also include nutrients for the spores, such as germination nutrients that allow germination and/or growth of any viable surviving spores. In some preferred embodiments, the solvent of the liquid composition is water. The combination of nutrients form a nutrient medium and together with the enzyme substrate and other non-nutrient components (such as indicators, buffer components, salts, etc., see below) form the liquid composition.

Suitable nutrients may be provided initially in a dry form (e.g., powdered form, tablet form, caplet form, capsule form, a film or coating, entrapped in a bead or other carrier, another suitable shape or configuration, or a combination thereof) and then combined with a suitable solvent to provide a liquid composition that is then placed in the actuatable container.

The nutrients in the liquid medium can include one or more sugars, including, but not limited to, glucose, fructose, dextrose, maltose, trehalose, cellibiose, or the like, or a combination thereof. Alternatively, the nutrients may include complex media, such as peptone, tryptone, phytone peptone, yeast extract, soybean casein digest, other extracts, hydrolysates, etc., or a combination thereof. In other embodiments, the nutrients in the liquid composition represent a combination of one or more complex media components and other specific nutrients. The nutrient medium can also include a salt, including, but not limited to, sodium chloride, potassium chloride, calcium chloride, or the like, or a combination thereof. In some embodiments, the nutrient can further include at least one amino acid, including, but not limited to, at least one of methionine, phenylalanine, alanine, tyrosine, and tryptophan.

As part of a self-contained biological indicator, the liquid composition comprising nutrients, the enzyme substrate, and other components is typically present throughout the sterilization procedure but is kept separate and not accessible to the sources of biological activity in the actuatable container until desired. After the sterilization process is completed and the biological indicator is used to determine the efficacy of the sterilization, the liquid composition is placed in contact with the spores resulting in a mixture. In this disclosure, placing the liquid composition with the spores includes activating the actuatable container so that the liquid composition is released and contacts the spores. This process may include mixing of the liquid composition with the spores, such as manual or mechanical shaking of the housing of the biological indicator so that the liquid composition adequately mixes with the spores.

In this disclosure, the process of bringing the spores and medium together is referred to as "activation" of the biological indicator. That is, the term "activation" and variations thereof, when used with respect to a biological indicator refer generally to bringing one or more sources of biological activity (e.g., spores) in fluid communication with the liquid composition (comprising, e.g., a nutrient medium for the spores of interest and an enzyme substrate). For example, when an actuatable container within the biological indicator that contains the liquid composition is at least partially fractured, punctured, pierced, crushed, cracked, breaking, or the like, such that the medium has been put in fluid communication with the source(s) of biological activity, the biological indicator can be described as having been "activated." Said another way, a biological indicator has been activated when the source(s) of biological activity have been exposed to the liquid composition that was previously housed separately from the source(s) of biological activity.

In some preferred embodiments, the mixture resulting from mixing the liquid composition with the spores after activation remains isolated within the housing of the biological indicator after the sterilization cycle has been completed and no additional reagents or components are added to it during or after activation. If the spores are viable and grow, then the enzyme produced by the bacteria catalyzes the cleavage of the enzyme substrate, which produces the fluorescently detectable compound. This means that the same solution in the same container (housing) is used for three separate events: (a) spore germination/growth, if the spores are viable, (b) the enzymatic cleavage of the enzyme substrate, resulting in the production of the fluorescently-detectable compound, and (c) the fluorescence detection of the fluorescently-detectable compound.

The inventors have developed a liquid composition for the self-contained biological indicator such that the three events mentioned above can take place in the same container, using the same germination/growth solution for the cleavage and the florescence detection. In some embodiments, the inventors have established that in order to be able to determine the success of a given sterilization cycle, the pH of the mixture resulting from mixing the liquid composition and the spores is from 7.65 to 8.9. In other embodiments, the pH range is from 7.8 to 8.4. Surprisingly, this pH is not the optimum pH for growth, nor the optimum pH for the enzymatic cleavage, nor the optimum pH for detecting fluorescence. Yet, the inventors have demonstrated that, among other factors, when the pH of the mixture is between the range from 7.65 to 8.9, the self-contained biological indicator can successfully determine the success of a sterilization cycle, such as any of the steam sterilization cycles chosen from the powerset of the following eleven cycles: 121 gravity, 121 pre-vac, 121 SFPP, 132 gravity, 132 pre-vac, 132 SFPP, 134 pre-vac, 134 SFPP, 135 gravity, 135 pre-vac, and 135 SFPP, preferably within less than 1 hr, more preferably within less than 30 min.

Figure 4:
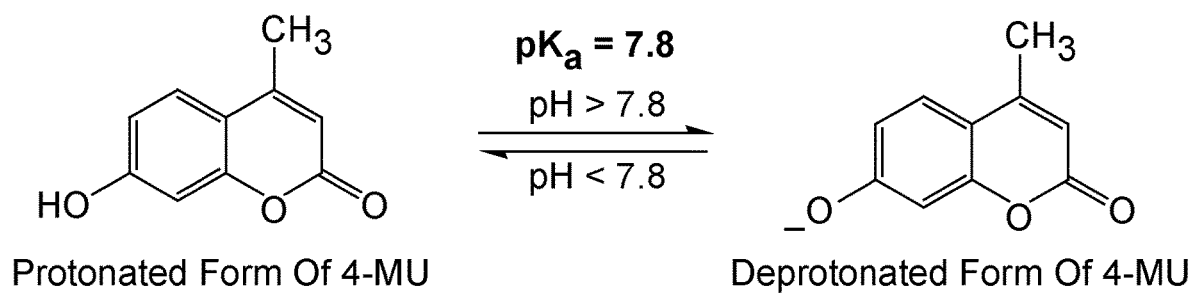
FIG. 4 shows the protonated and deprotonated forms of 4-methylumbelliferone (4-MU)

When the enzyme substrate 4-methylumbelliferyl-alpha-D-glucoside, which is hydrolyzed by an enzyme (e.g., alpha-D-glucosidase) to produce 4-MU as the fluorescently detectable compound, the inventors discovered that the fluorescence intensity can be explained in terms of the relative proportion of the protonated and deprotonated forms of the hydroxyl group of 4-MU. The protonated and the deprotonated forms of the hydroxyl group of 4-MU are in equilibrium with a pKa of 7.8 (FIG. 4). When the pH is lower than the pKa, the protonated form is predominant, and when the pH is higher than the pKa, the deprotonated form is predominant.

The inventors have found that in articles and methods of the present disclosure, wherein the enzyme substrate comprises a fluorophore component that; when separated from the enzyme substrate by the enzyme, consists of 7-hydroxy-2H-chromen-2-one or a derivative thereof; and wherein the initial pH of the mixture formed of the liquid composition and the source of biological activity is greater than or equal to the pKa of the 7-hydroxy-2H-chromen-2-one or the derivative thereof, the source of biological activity can be detected more rapidly after exposure to a sterilization process even though a pH above 7.8 is not optimal for germination of spores, growth of most vegetative test microorganisms, or most enzyme activities used for determining the effectiveness of a sterilization process.

Suitable fluorophore components include, but are not limited to fluorophore components selected from the group consisting of 4-methyl-5-fluoro-2H-chromen-2-one, 4-methyl-6-fluoro-2H-chromen-2-one, 4-methyl-8-fluoro-2H-chromen-2-one, 4-methyl-6,8-difluoro-2H-chromen-2-one, 4-methyl-6-chloro-2H-chromen-2-one, and 4-methyl-ethanoate-6-fluoro-2H-chromen-2-one.

In some embodiments, the liquid composition may comprise a buffered solution. The ionic conditions of the buffered solution should be such that the enzyme and enzyme substrate are not affected. In some embodiments, a buffer solution is used as part of the liquid composition, such as phosphate buffers, (e.g., phosphate buffered saline solution, potassium phosphate or potassium phosphate dibasic), tris (hydroxymethyl) aminomethane-HCl solution, or acetate buffer, or any other buffer suitable for sterilization known in the art. Buffers suitable for the present biological indicators should be compatible with fluorogenic and chromogenic enzyme substrates used as part of the liquid composition. Another consideration in choosing the buffers is their influence on the enzyme activity. For example, phosphate buffered saline contains a relatively high concentration of inorganic phosphate, which is a competitive inhibitor of alkaline phosphatase. Thus, for that enzyme, a Tris-HCl buffer is recommended. The strength of the buffered solution may be from 0.05 M to 0.5 M, preferably from 0.05 M to 0.25 M, more preferably from 0.05 M to 0.15 M, even more preferably about 0.1 M.

The concentration of enzyme substrate present in the liquid composition depends upon the identity of the particular substrate and enzyme, the amount of enzyme-product that must be generated to be detectable, either visually or by instrument, and the amount of time that one is willing to wait in order to determine whether active enzyme is present in the reaction mixture. Preferably, the amount of enzyme substrate is sufficient to react with any residual active enzyme present, after the sterilization cycle, within about an eight-hour period of time, such that at least $10^{-8}$ molar enzyme-modified product is produced. In cases where the enzyme substrate is a 4-methylumbelliferyl derivative, the inventors have been found that its concentration in the aqueous buffered solution is preferably between about $10^{-5}$ and $10^{-3}$ molar. Although the use of a buffered solution may aid in providing stable reaction conditions for the enzyme and its substrate, the inventors were able to successfully detect biological activity (spore germination and growth) in conditions without the use of a buffered solution. Accordingly, in some embodiments, the liquid composition only comprises a solution adjusted to a suitable pH, but without an added buffer system. In other embodiments, however, the liquid composition does comprise a buffered solution.

In some embodiments, the biological indicator may comprise an additional indicator compound that can facilitate the detection of another metabolic activity of the test microorganisms (e.g., spore) (aside from an enzyme substrate that can produce a fluorescently detectable compound). This additional metabolic activity can also be an enzymatic activity. Non-limiting examples of indicator compounds include a chromogenic enzyme substrate (e.g., observable in the visible spectrum), a pH indicator, a redox indicator, a chemiluminescent enzyme substrate, a dye, and a combination of any two or more of the foregoing indicator compounds.

In some embodiments, the additional indicator is a pH indicator that produces a change in color when the pH decreases, indicating growth of the test microorganisms. In some embodiments, the pH indicator is bromocresol purple. The pH indicator can be used to detect a second biological activity, such as the fermentation of a carbohydrate to acid end products (suggesting survival of the test microorganisms) and an enzymatic biological activity such as α-D-glucosidase enzyme activity, for example. These activities can indicate the presence or absence of a viable spore following the exposure of a biological indicator to a sterilization process, for example. The bromocresol purple can be used at a concentration of about 0.03 g/L in the aqueous mixture, for example. The 4-methylumbelliferyl-α-D-glucoside can be used, for example, at a concentration of about 0.05 to about 0.5 g/L (e.g., about 0.05 g/L, about 0.06 g/L, about 0.07 g/L, about 0.08 g/L, about 0.09 g/L, about 0.1 g/L, about 0.15 g/L, about 0.2 g/L, about 0.25 g/L, about 0.3 g/L, about 0.35 g/L, about 0.4 g/L, about 0.45 g/L, about 0.5 g/L) in the aqueous mixture.

The combination of bromocresol purple and 4-methylumbelliferyl-α-D-glucoside represents a preferred combination of enzymatic substrate and additional indicator according to the present disclosure, but other combinations are contemplated within the scope of the present disclosure. In yet other embodiments, the biological indicator does not comprise a pH indicator.

In some situations, one or more components of a biological indicator (e.g., crevasses in the housing, substrates or carriers for spores, walls of container, etc.) may retain residual oxidizing sterilant. This can occur, for example, with hydrogen peroxide vapor as well as with other vapor sterilants such as ozone and peracetic acid. For example, certain carrier materials, e.g., those that are hydrophilic such as glass fiber and cellulosic materials, can retain residual oxidizing sterilant, particularly hydrogen peroxide. In this context, "residual" means an amount of retained sterilant that inhibits the growth of low numbers of spore survivors. Typically, this means more than 10 micrograms of sterilant retained per microgram of carrier. In certain situations, the amount of residual sterilant can be greater than 40 micrograms sterilant per milliliter of growth media. As a comparison, if the carrier material has a contact angle of greater than 90°, it is hydrophobic, and there is generally no more than 10 micrograms sterilant retained per microgram of carrier.

Therefore, in some embodiments, the biological indicators comprise one or more neutralizers, which are not an enzyme and not a metal catalyst disposed within the biological indicator. A neutralizer is a compound or material that reacts with residual sterilant, e.g., hydrogen peroxide, to neutralize its effect, wherein the neutralizer is not an enzyme, and not a metal catalyst. Enzyme neutralizers are typically not stable at the high temperatures, and thus not desirable.

Suitable examples of neutralizers include sulfur containing materials such as methionine, L-cysteine, D-ethionine, S-methyl-L-cysteine, S-benzyl-L-cysteine, sodium thiosulfate, glutathione, L-cystathionine, N-acetyl-L-cysteine, carboxymethylcysteine, D,L-homocysteine, D,L-homocysteine-thiolactone, and thiodipropionic acid, and non-sulfur containing materials such as isoascorbic acid, potassium ferricyanide, and sodium pyruvate. Various combinations of such neutralizers can be used. Preferred neutralizers include methionine, L-cysteine, D-ethionine, S-methyl-L-cysteine, S-benzyl-L-cysteine, sodium thiosulfate, thiodipropionic acid, isoascorbic acid, potassium ferricyanide, sodium pyruvate, and combinations thereof.

Detection of Enzymatic Activity and Determination of a Successful Sterilization Process In another aspect, the present disclosure provides a method for determining the efficacy of a sterilization process. In any embodiment, the method comprises exposing a source of biological activity to the sterilization process. The source of biological activity can be any suitable source of biological activity (e.g., test microorganisms, spores, an enzyme activity) described herein. The source of biological activity can be disposed in any embodiment of a sterilization process indicator disclosed herein. Alternatively, the source of biological activity can be disposed in a container (e.g., a tube) or on a substrate (e.g., a paper strip, a glass slide, or yarn). Exposing the source of biological activity to the sterilization process comprises placing the article on which (or in which) the source of biological activity is disposed into a vessel (e.g., an automated sterilizer) in which the sterilization process is conducted.

In any embodiment of the method, the source of biological activity comprises and/or is capable of producing an enzyme capable of reacting with a fluorogenic enzyme substrate to produce a fluorescent product as described herein.

After exposing the source of biological activity to the sterilization process, the method comprises bringing the source of biological activity into contact with a liquid composition. The liquid composition can be any suitable liquid composition (e.g., an aqueous liquid composition) according to the present disclosure. Bringing the source into contact with the liquid composition comprises placing the source of biological activity in liquid contact with the fluorogenic enzyme substrate. In certain embodiments wherein the source of biological activity is disposed in a container (e.g., a tube), placing the source of biological activity in liquid contact with the fluorogenic enzyme substrate can comprise adding (e.g., by pipet) the liquid composition to the container containing the source of biological activity. In certain embodiments wherein the source of biological activity is disposed in a self-contained sterilization process indicator according to the present disclosure, placing the source of biological activity in liquid contact with the fluorogenic enzyme substrate can comprise actuating the container to release the liquid composition as described herein. Optionally, after placing the source of biological activity in liquid contact with the fluorogenic enzyme substrate, the components can be mixed (e.g., by manual or mechanical agitation or vortex action). After bringing the source into contact with the liquid composition, a resulting mixture of the source of biological activity and the liquid composition has an initial pH in the range from 7.65 to 8.9. In some embodiments, the resulting liquid mixture has an initial pH in the range is from 7.8 to 8.4.

After bringing the source of biological activity into contact with the liquid composition, the method comprises incubating the mixture for a period of time. Incubating the mixture for a period of time comprises incubating the mixture at a specified temperature. The specified temperature can be any suitable incubation temperature described herein for the test microorganism and/or the enzyme activity. The period of time can be any suitable period of time of incubation described herein. In certain embodiments, the specified period of time is less than 8 hours, in some embodiments, less than 1 hour, in some embodiments, less than 30 minutes, in some embodiments, less than 15 minutes, in some embodiments, less than 5 minutes, and in some embodiments, less than 1 minute. In other embodiments, the suitable incubation time for the biological indicator of this disclosure is from 10 min to 1 hr, or from 10 min to 50 min, or from 10-30 min, or from 10-20 min, or form 10-25 min, or from 15 to 30 min, or from 15-25 min, or from 15-20 min.

During and/or after incubating the mixture for a period of time, the method comprises detecting the fluorescent product formed in the mixture. Detecting the fluorescent product comprises directing electromagnetic radiation (e.g., radiation within the ultraviolet spectrum of electromagnetic energy) into the mixture and detecting electromagnetic radiation (e.g., radiation within the ultraviolet spectrum or visible spectrum of electromagnetic energy) emitted by the fluorescent product in the mixture, as described herein. In certain embodiments, detecting electromagnetic radiation emitted by the fluorescent product comprises detecting electromagnetic radiation using an automated detector (e.g., an auto-reader as described herein).

In any embodiment, detecting the fluorescent product comprises detecting a quantity of fluorescence emitted by the fluorescent product. In any embodiment, the quantity of fluorescence detected can be compared to a threshold quantity. In any embodiment, a first quantity of fluorescence detected after a first specified time period can be compared to a second quantity of fluorescence detected after a second specified time period. In certain embodiments, detecting at least a threshold quantity of the fluorescent product indicates a lack of efficacy of the sterilization process.

In certain embodiments, a method according to the present disclosure can be used to determining efficacy of a sterilization process that uses a sterilant selected from the group consisting of steam, ethylene oxide gas, hydrogen peroxide vapor, methyl bromide, chlorine dioxide, formaldehyde, peracetic acid, ozone, ionizing radiation, and a combination of any two or more of the foregoing sterilants.

As mentioned in the previous section, after the indicator is exposed to the sterilization process, the spores can be incubated in a nutrient medium to determine whether any of the spores survived the sterilization process, with spore growth indicating that the sterilization process was insufficient to destroy all of the test microorganisms.

In some embodiments, the cap of the biological indicator can be coupled to the body of the biological indicator during sterilization in a first position that maintains fluid communication between the interior of the biological indicator and ambience, allowing the sterilant to reach the interior of the biological indicator. After sterilization, in order to activate the biological indicator, the cap can be pressed further onto the tube (e.g., to a second position in which the interior of the biological indicator is no longer in fluid communication with ambience) to maintain sterility and reduce the evaporation rate of the liquid composition. As mentioned previously, the liquid composition is maintained separate from the spores in the actuatable container during sterilization but is released into the interior of the housing after sterilization as part of the activation by fracturing, puncturing, piercing, crushing, cracking, breaking, or the like, the actuatable container.

In some embodiments of the present disclosure, closing the biological indicator (e.g., moving a portion of the biological indicator, such as the cap, relative to another portion to seal the interior) can include or cause fracturing, puncturing, etc. of the actuatable container containing the liquid composition, such that closing the biological indicator causes activation of the biological indicator.

After activation, the mixture resulting from placing the liquid composition in contact with the spores is incubated is continued for a period of time and under conditions that would be sufficient to liberate a detectable amount of the enzyme modified product, assuming, of course, that any of the spores remains active. In general, the amount of product which is detectable by known methods is at least $10^{-8}$ molar. Preferably, the incubation conditions are sufficient to generate at least $10^{-8}$ molar of fluorescently detectable compound, more preferably, about $10^{-6}$ molar to $10^{-5}$ molar of fluorescently detectable compound. The incubation time and temperature needed to produce a detectable amount of fluorescently detectable compound will depend upon the identity of the enzyme and the substrate, and the concentrations of each present in the reaction mixture. In general, the incubation time required is between about 1 minute and 12 hours, and the incubation is between about 20° and 70° C. Preferably, where *Bacillus subtilis* or *Geobacillus stearothermophilus* is the source of the enzyme, the incubation time is from about 10 minutes and 3 hours, or from 10 minutes to 1 hour, or from 15 minutes and 1 hour, or from 15 minutes and 30 minutes, or from 15 minutes to 25 minutes, and the incubation temperature is from about 30° and 40° C., and from about 52° to 65° C., respectively.

To detect a detectable change in the spores the biological indicator can be assayed immediately after the liquid composition and the spores have been combined to achieve a baseline reading. After that, any detectable change from the baseline reading can be detected. The biological indicator can be monitored and measured continuously or intermittently. In some embodiments, a portion of, or the entire, incubating step may be carried out prior to measuring the detectable change. In some embodiments, incubation can be carried out at one temperature (e.g., at 37° C., at 50-60° C., etc.), and measuring of the detectable change can be carried out at a different temperature (e.g., at room temperature, 25° C., or at 37° C.). In other embodiments, the incubation and measurement of fluorescence occurs at the same temperature.

The readout time of the biological indicator (i.e., the time to determine the effectiveness of the sterilization process) can be, in some embodiments, less than 8 hours, in some embodiments, less than 1 hour, in some embodiments, less than 30 minutes, in some embodiments, less than 15 minutes, in some embodiments, less than 5 minutes, and in some embodiments, less than 1 minute. In other embodiments, the readout time for the biological indicator of this disclosure is from 10 min to 1 hr, or from 10 min to 50 min, or from 10-30 min, or from 10-20 min, or form 10-25 min, or from 15 to 30 min, or from 15-25 min, or from 15-20 min. The detection of fluorescence above the baseline reading that would indicate presence of viable spores (i.e., a failed sterilization process) can be performed according to any method know in the art, including area under curve (in a plot of time vs fluorescence intensity), monitoring a change in slope of the curve, using a threshold value for the fluorescence, etc., or a combination thereof of two or more techniques.

One of the advantages of the biological indicators of this disclosure is that a single type can be used for various sterilization conditions. The working examples below show a single type of biological indicator can be used for all of the following steam sterilization cycles: 121 gravity, 121 pre-vac, 121 SFPP, 132 gravity, 132 pre-vac, 132 SFPP, 134 pre-vac, 134 SFPP, 135 gravity, 135 pre-vac, and 135 SFPP. For that reason, the biological indicator can be used for any subset of cycles chosen from the set above. That is, a single biological indicator is capable of determining the efficacy of one or more sterilization cycles chosen from the powerset of 121 gravity, 121 pre-vac, 121 SFPP, 132 gravity, 132 pre-vac, 132 SFPP, 134 pre-vac, 134 SFPP, 135 gravity, 135 pre-vac, and 135 SFPP.

In addition to being able to determine the efficacy of any of the above sterilization cycles, the biological indicator is capable of doing so in less than one hour. In fact, in some embodiments, the biological indicator has a readout time of less than 1 hour, in some embodiments, less than 30 minutes, in some embodiments, less than 15 minutes, in other embodiments, the readout time is from 10 min to 1 hr, or from 10 min to 50 min, or from 10-30 min, or from 10-20 min, or form 10-25 min, or from 15 to 30 min, or from 15-25 min, or from 15-20 min.

Exemplary Embodiments of Self-Contained Biological Indicators

Figure 2:
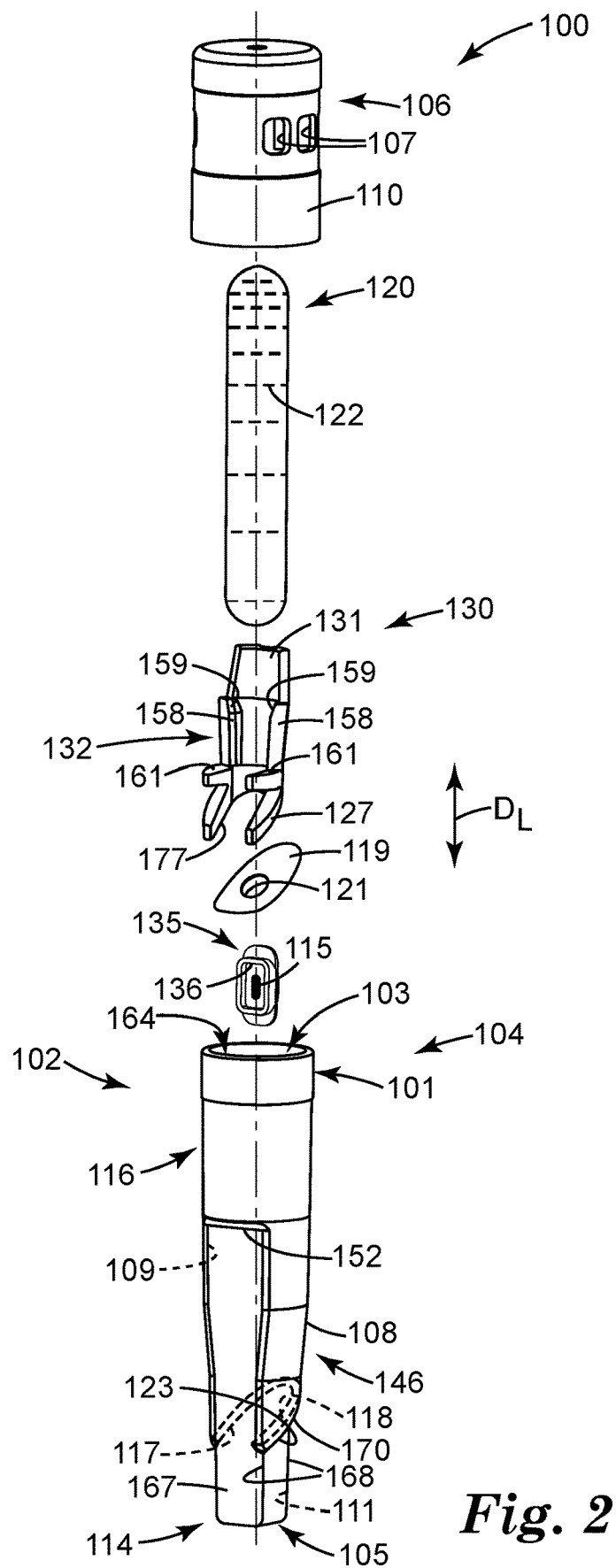
FIG. 2 represents an expanded view of an exemplary biological indicator of the present disclosure.

Turning now to FIGS. 1 and 2, an exemplary biological indicator 100 can include a housing 102, which can include a first portion 104 and a second portion 106 (e.g., a cap) adapted to be coupled together to provide a self-contained biological indicator. In some embodiments, the first portion 104 and second portion 106 can be formed of the same materials, and in some embodiments, the first portion 104 and the second portion 106 can be formed of different materials. The housing 102 can define a reservoir 103 of the biological indicator 100 in which other components can be positioned and into which a sterilant can be directed during a sterilization process.

The housing 102 can be defined by at least one liquid impermeable wall, such as a wall 108 of the first portion 104 and/or a wall 110 of the second portion 106. It should be understood that a one-part unitary housing 102 may also be employed or that the first and second portions 104 and 106 can take on other shapes, dimensions, or relative structures without departing from the spirit and scope of the present disclosure. Suitable materials for the housing 102 (e.g., the walls 108 and 110) can include, but are not limited to, a glass, a metal (e.g., foil), a polymer (e.g., polycarbonate (PC), polypropylene (PP), polyphenylene (PPE), polyethylene, polystyrene (PS), polyester (e.g., polyethylene terephthalate (PET)), polymethyl methacrylate (PMMA or acrylic), acrylonitrile butadiene styrene (ABS), cyclo olefin polymer (COP), cyclo olefin copolymer (COC), polysulfone (PSU), polyethersulfone (PES), polyetherimide (PEI), polybutyleneterephthalate (PBT)), a ceramic, a porcelain, or combinations thereof.

In some embodiments, the biological indicator 100 can further include an actuatable container 120 that contains a liquid (e.g., liquid composition) 122, and which is dimensioned to be received within the biological indicator 100, for example, within at least a portion of the housing 102 (e.g., at least within the first portion 104 of the housing 102). The actuatable container 120 can be formed of a variety of materials, including, but not limited to, one or more of metal (e.g., foil), a polymer (e.g., any of the polymers listed above with respect to the housing 102), glass (e.g., a glass ampoule), and combinations thereof. In some embodiments, only a portion of the container 120 is frangible, for example, the container 120 can include a frangible portion or cover (e.g., a frangible barrier, film, membrane, or the like). The actuatable container 120 can have a first state in which it is intact and the liquid 122 is contained therein, and a second state in which at least a portion of the container 120 is fractured. In the second state of the container 120, the liquid 122 can be in fluid communication with the reservoir 103 of the biological indicator 100, e.g., when the container 120 is positioned in the biological indicator 100.

As shown in the illustrated embodiment in FIGS. 1 and 2, the container 120 can be held in place within the biological indicator 100 and/or fractured by an insert 130.

The first portion 104 of the housing 102 can be adapted to house a majority of the components of the biological indicator 100, and can be referred to as the "body," or "tube," "tubular body," "base," or the like. The housing 102 can include a reservoir 103 that can be defined by one or both of the first portion 104 and the second portion 106 of the housing 102. The biological indicator 100 can further include spores or another source(s) of biological activity 115 (or a locus of spores) positioned in fluid communication with the reservoir 103. As shown in FIGS. 1-2, the second portion 106 of the housing 102 can include one or more apertures 107 to provide fluid communication between the interior of the housing 102 (e.g., the reservoir 103) and ambience. For example, the one or more apertures 107 can provide fluid communication between the spores 115 and ambience during a sterilization process and can serve as an inlet into the biological indicator 100 and as an inlet of a sterilant path 164 (described in greater detail below). In some embodiments, the second portion 106 of the housing 102 can be coupled to a first (e.g., open) end 101 of the first portion 104 of the housing 102, and the spores 115 can be positioned at a second (e.g., closed) end 105, opposite the first end 101, of the first portion 104 of the housing 102.

In some embodiments, a barrier or filter (e.g., a sterile barrier; not shown) can be positioned in the sterilant path 164 (e.g., at the inlet formed by the aperture 107) to inhibit contaminating or foreign organisms, objects or materials from entering the biological indicator 100. Such a barrier can include a gas-transmissive, microorganism-impermeable material, and can be coupled to the housing 102 by a variety of coupling means, including, but not limited to, an adhesive, a heat seal, sonic welding, or the like. Alternatively, the barrier can be coupled to the sterilant path 164 via a support structure (such as the second portion 106) that is coupled to the first portion 104 of the housing 102 (e.g., in a snap-fit engagement, a screw-fit engagement, a press-fit engagement, or a combination thereof). During exposure to a sterilant, the sterilant can pass through the barrier into the sterilant path 164 and into contact with the spores 115.

In some embodiments, as shown in the illustrated embodiments, the housing 102 can include a lower portion 114 and an upper portion 116, which can be at least partially separated by an inner wall (or partial wall) 118, ledge, partition, flange, or the like, in which can be formed an opening 117 that provides fluid communication between the lower portion 114 and the upper portion 116. In some embodiments, the lower portion 114 of the first portion 104 of the housing 102 (sometimes referred to as simply "the lower portion 114" or the "the lower portion 114 of the housing 102") can be adapted to house the spores 115 or a locus of spores. In some embodiments, the lower portion 114 can be referred to as the "detection portion" or "detection region" of the housing 102, because at least a portion of the lower portion 114 can be interrogated for signs of spore growth. In addition, in some embodiments, the upper portion 116 of the first portion 104 of the housing 102 (sometimes referred to as "the upper portion 116" or the "the upper portion 116 of the housing 102" for simplicity) can be adapted to house at least a portion of the actuatable container 120, particularly before activation.

In some embodiments, the portion of the reservoir 103 that is defined at least partially by the upper portion 116 of the housing 102 can be referred to as a first chamber (or reservoir, zone, region, or volume) 109 and the portion of the reservoir 103 that is defined at least partially by the lower portion 114 of the housing 102 can be referred to as a second chamber (or reservoir, zone, region, or volume) 111. In some embodiments, the second chamber 111 can be referred to as a "spore growth chamber" or a "detection chamber," and can include a volume to be interrogated for spore viability to determine the efficacy of a sterilization process.

The first chamber 109 and the second chamber 111 can be positioned in fluid communication with each other to allow a sterilant and the liquid 122 to move from (i.e., through) the first chamber 109 to the second chamber 111. In some embodiments, the degree of fluid connection between the first chamber 109 and the second chamber 111 (e.g., the size of an opening, such as the opening 117, connecting the first chamber 109 and the second chamber 111) can increase after, simultaneously with, and/or in response to the activation step (i.e., the liquid 122 being released from the container 120). In some embodiments, the control of fluid communication (or extent of fluid connection) between the first chamber 109 (e.g., in the upper portion 116) and the second chamber 111 (e.g., in the lower portion 114) can be provided by at least a portion of the insert 130.

The container 120 can be positioned and held in the first chamber 109 during sterilization and when the container 120 is in a first, unfractured, state. The spores 115 can be housed in the second chamber 111 and in fluid communication with ambience when the container 120 is in the first state. The first chamber 109 and the second chamber 111 can be configured such that the container 120 is not present in the second chamber 111, and particularly, not when the container 120 is in its first, unfractured, state. A sterilant can move into the second chamber 111 (e.g., via the first chamber 109) during sterilization, and the liquid 122 can move into the second chamber 111 (e.g., from the first chamber 109) during activation, when the container 120 is fractured and the liquid 122 is released into the interior of the housing 102.

As a result, when the container 120 is in the first state, the first chamber 109 and the second chamber 111 can be in fluid communication with one another, and with ambience (e.g., during sterilization). For example, the first chamber 109 and the second chamber 111 can be in fluid communication with ambience via the one or more apertures 107. In some embodiments, the first chamber 109 and the second chamber 111 can be in fluid communication with ambience in such a way that the first chamber 109 is positioned upstream of the second chamber 111 when a sterilant is entering the biological indicator 100. That is, the first chamber 109 can be positioned between the sterilant inlet (e.g., the one or more apertures 107) and the second chamber 111, and the sterilant inlet can be positioned on an opposite side of the first chamber 109 than the second chamber 111.

Systems

In another aspect, the present disclosure provides a system that can be used for determining the efficacy of a sterilization process. The system comprises any embodiment of the self-contained biological indicator according to the present invention, and an automated reader. The automated reader is configured to i) receive at least a portion of the biological indicator, ii) direct a first wavelength of electromagnetic radiation into the liquid composition in the housing, and iii) detect or measure a quantity of a second wavelength of electromagnetic radiation emitted by the fluorescent product. Accordingly, a person having ordinary skill in the art will recognize the automated reader comprises inter alia a locus (e.g., a chamber) dimensioned to receive the biological indicator, a source of ultraviolet electromagnetic radiation, a photodetector for detecting and measuring fluorescence emitted from the biological indicator, at least one microprocessor for controlling components of the automated reader. Optionally, the automated reader further comprises software or firmware comprising an algorithm for identifying biological indicators that exhibit fluorescence indicative of complete inactivation the source of biological activity or survival of at least a portion of the source of biological activity after exposure to a sterilization process.

In any embodiment of the system, the self-contained biological indicator is adapted, as disclosed herein, to be used to determine efficacy of any steam sterilization process selected from the group consisting of 121° C. gravity process, 121 C pre-vac process, 121 C SFPP process, 132 C gravity process, 132 C pre-vac process, 132 C SFPP process, 134 C pre-vac process, 134 C SFPP process, 135 C gravity process, 135 C pre-vac process, and 135 C SFPP process.

Kits

In another aspect, the present disclosure provides a kit that can be used for determining the efficacy of a sterilization process. In one embodiment, the kit comprises i) a source of biological activity comprising and/or capable of producing an enzyme capable of catalyzing the cleavage of an enzyme substrate, ii) the enzyme substrate, iii) a liquid composition comprising the enzyme substrate, and an effective amount of an acidic component and/or a basic component such that, when the source of biological activity and the liquid composition are combined, a resulting mixture of the source of biological activity and the liquid composition has an initial pH in the range from 7.65 to 8.9. A product of the cleavage of the enzyme substrate by the enzyme can be detected by its fluorescence. When the liquid composition is brought into contact with the source of biological activity and the effective amount of the acidic component and/or the basic component, a resulting mixture of the liquid composition, the source of biological activity and the effective amount of the acidic component and/or the basic component has an initial pH in the range from 7.65 to 8.9.

In another embodiment, the kit comprises any embodiment of the self-contained biological indicator of the present disclosure.

In any embodiment of the kit, the source of biological activity comprises an isolated enzyme or a plurality of bacterial spores.

EXAMPLES

Equipment:

The sterilizer(s) used in each study is/are listed in each respective Example. For $H_2O_2$ sterilization processes, one or more of the following sterilizers was used as indicated in each Example: a STERRAD® 100NX System available from Advanced Sterilization Products, Irvine, Calif.; a STERRAD® 100 S System available from Advanced Sterilization Products, Irvine, Calif.; and/or a STERILUCENT™ PSD-85 Sterilizer available from Sterilucent, Inc., Minneapolis, Minn. For steam sterilization processes, one or more of the following sterilizers was used as indicated in each Example: a steam resistometer available from H & W Technology, Rochester, N.Y.; and an AMSCO 3013C sterilizer.

Commercial auto-readers were used to detect fluorescence in biological indicators. The auto-reader used in each study is listed in each respective Example. For $H_2O_2$ sterilization processes, a 3M™ Attest™ 490H Auto-reader (3M Company, St. Paul, Minn.) was used. For steam sterilization processes, a 3M™ Attest™ 490 Auto-reader (3M Company, St. Paul, Minn.) was used.

Example 1: Preparation of Biological Indicators

Spore Carrier Preparation

*Geobacillus stearothermophilus* spore crops were produced using a tryptone Soy broth media by 3M production facilities. After harvesting, spore crops were washed by centrifugation and suspended in deionized water or different concentration 0.01 M potassium phosphate buffer at different pH targets to make spore coating solutions. The spore coating solutions were coated onto spore carriers (shown and described in U.S. Pat. No. 10,047,334; which is incorporated herein by reference in its entirety) with a spore minimum recovery population target of $1\times10^6$ colony forming units per carrier (CFU/carrier). Carriers were used in the assembly of the self-contained biological indicator as described below.

Preparation of Liquid Composition

A complex nutrient medium; suitable for germinating, growing and detecting growth of *Geobacillus stearothermophilus* spores; was used in the self-contained biological indicators used to monitor steam sterilization processes. The medium comprised deionized water, peptones, amino acids, a fermentable carbohydrate, bromocresol purple, and 300 mg/L MUG. The pH of the nutrient medium was adjusted with HCl or NaOH, as needed, unless noted otherwise. Each ampoule contained about 0.5 ml, of nutrient medium.

A similar medium was used in the self-contained biological indicators used to monitor hydrogen peroxide sterilization processes, with the exception that the liquid composition further comprised a neutralizer compound (L-methionine) as described in U.S. Pat. No. 8,975,067; which is incorporated herein by reference in its entirety.

The nutrient media were prepared, aliquoted into glass ampoules (0.5 mL per ampoule) and autoclaved before being used in the assembly of the self-contained biological indicators.

Assembly of Self-Contained Biological Indicators

The self-contained biological indicators were assembled as described in U.S. Pat. No. 10,047,334 using the components as shown and described therein.

Example 2: Effect of Spore Coating pH on Detection of Spore Survival After Exposure to an $H_2O_2$ Sterilization Process The impact of spore coating solution pH was investigated. The fluorescence signal as detected in the 490H Auto-readers (available from 3M Company, St. Paul, Minn.) was analyzed after exposure to hydrogen peroxide sterilant.

Biological Indicators were prepared using spores that were suspended in phosphate buffers at different pH values as described above. The biological indicators were exposed to sub-lethal hydrogen peroxide sterilant doses using in a STERRAD 100NX sterilizer. After, exposure to the hydrogen peroxide, the biological indictors were activated (by breaking the ampoule and causing the liquid composition to contact the spores) and incubated in 490H Auto-readers. The auto-readers were configured to record the time it took to detect positive fluorescence in each biological indicator. Data showing the time-to-turn fluorescence positive are presented in Table 1.

The biological indicators were exposed to a sub-lethal hydrogen peroxide sterilization process (i.e., at least some spores survived in some of the biological indicators exposed to some of these processes) in a commercial sterilizer (STERRAD 100NX sterilizer).

TABLE 1

Spore coating pH effects on time-to-turn fluorescence positive result

| | Spore Coating Solution Buffer pH | | |
|---|---|---|---|
| | pH 6.0 | pH 7.0 | pH 8.0 |
| Time to result (minutes) | 19 ± 55 | 21 ± 57 | 8 ± 9 |

From among the buffers tested, the data comparison showed the biological indicators with spore coating solution buffers adjusted to pH 8 had the fastest time-to-turn fluorescence positive result with better consistency and no tailing effect or stragglers. In comparison, the spore coatings buffered at pH 6 or pH 7 had higher standard deviations.

Example 3: Effect of Ampoule Media pH on Detection of Spore Survival After Exposure to an $H_2O_2$ Sterilization Process Ampoule media of different pH values were produced with the pH adjusted using sodium hydroxide and hydrochloric acid. Biological Indicators were prepared using ampoules containing the pH-adjusted media.

The biological indicators were exposed to a sub-lethal dose of hydrogen peroxide sterilant in a STERRAD 100NX $H_2O_2$ sterilizer. After, exposure to the hydrogen peroxide, the biological indicators were activated (by breaking the ampoule and causing the liquid composition to contact the spores) and incubated in 490H Auto-readers. The auto-readers were configured to record the time it took to detect positive fluorescence in each biological indicator. Representative time-to-turn fluorescence positive data are presented in Table 2.

TABLE 2

Ampoule media pH effects on the time it takes for a positive result (TTR)

| | Ampoule media pH | | |
|---|---|---|---|
| | pH 7.5 | pH 8.0 | pH 9.0 |
| Time to result (minutes) | 33 ± 43 | 6 ± 3 | 50 ± 85 |

These comparison data showed the biological indicators with ampoule media adjusted to pH 8 had the fastest time-to-turn fluorescence positive with better consistency and no tailing effect or stragglers, as indicated by the relatively low standard deviation. In comparison, the ampoule media with pH 7 and pH 9 had higher standard deviations.

Reference Example 1. Effect of pH on the Conversion of MUG to 4-MU by α-Glucosidase Activity in Spores Spore strips and nutrient medium, prepared as described in Example 1, were placed at the bottom of NMR tubes. 1 mL of nutrient media with a pH value as indicated in Table 3 was transferred to each of the NMR tubes. Deuterium water reference was inserted into the NMR tube for NMR locking and shimming without perturbing or diluting the BI solution. The NMR tube was quickly transferred to the NMR instrument and equilibrated at 60° C. Both MUG and 4-MU spectra were assigned based on their individual $^1$H-NMR characteristics and the yields of 4-MU after various periods of incubation were obtained by its proton NMR integration values in comparison with the proton integration values of MUG. Proton spectra were then acquired every 5-20 minutes until the reaction was >65% complete. Data from Table 3 demonstrates that the enzymatic activity was surprisingly retained at pH=8, but significantly decreased at pH=9, and the enzyme essentially became deactivated at pH=10.

TABLE 3

Effect of pH effect on the enzymatic conversion of MUG to 4-MU by spores after various periods of incubation at 60° C.

| Ampoule media pH | MUG to 4-MU (%) After 90 minutes | MUG to 4-MU (%) After 120 minutes | MUG to 4-MU (%) After 180 minutes | MUG to 4-MU (%) After 240 minutes |
|---|---|---|---|---|
| 7 | 16 | 20 | 34 | 51 |
| 8 | 17 | 20 | 34 | 58 |
| 9 | 3 | 7 | 12 | 20 |
| 10 | 0 | 0 | 0 | 0 |

Table 3 shows the enzymatic conversion of MUG to 4-MU does not change significantly between pH 7 and 8 even though the fluorescence signal intensity does. These results support the idea that the increase in fluorescent signal observed when changing the media pH from 7 and 8 is likely due to the shift in 4-MU equilibrium from the protonated to the deprotonated form and not to an increase in MUG conversion to 4-MU.

Example 4: Effect of Nutrient Medium pH on the Detection of Spore Survival After Exposure to an $H_2O_2$ Sterilization Process Biological indicators with ampoules containing nutrient medium were assembled as described in Example 1. The biological indicators were exposed for 1 minute to hydrogen peroxide ($H_2O_2$) in a STERRAD 100NX sterilizer. After the exposure, the ampoules were removed from the biological indicators and approximately 0.5 mL of nutrient medium (containing L-methionine and adjusted to the pH shown in Table 4) was added aseptically to individual biological indicators. The biological indicators were then immediately placed into a 490H Auto-reader that was configured to record the fluorescence Time To Result. The results are shown in Tables 4 and 5.

TABLE 4

Ampoule media pH effects on biological indicator performance in a $H_2O_2$ sterilizer

| Media | Fluorescence Result | pH Color Change Result | Visual Color Change Result | Time to Result (Minutes) |
|---|---|---|---|---|
| pH 6.02 | 0*/3 | 3/3 | Pale yellow | >240 |
| pH 7.00 | 3/3 | 3/3 | Bright yellow | 167 +/− 60 |
| pH 7.36 | 3/3 | 3/3 | Bright Yellow | 32 +/− 0 |
| pH 8.02 | 3/3 | 3/3 | Bright Yellow | 13 +/− 2 |
| pH 9.02 | 0/3 | 3/3 | Dark yellow/brown | >240 |

*A value of 0 indicates a negative fluorescence result after 240 minutes per a 490 H Auto-reader.

TABLE 5

Time to result data for biological indicators exposed to a 1-minute sterilization cycle in an $H_2O_2$ sterilizer

| Media pH | pH 8.0 | pH 8.2 | pH 8.4 | pH 8.6 |
|---|---|---|---|---|
| Time to Result (minutes) | 9 ± 5 | 18 ± 20 | 12 ± 11 | 56 ± 97 |

Optimum pH range for detection of surviving spores is greater than or equal to pH 8.0 and less than pH 8.6.

Example 5: Combined Effects of pH Adjustment of Spore Coatings and Liquid Medium on Fluorescent Detection of Surviving Spores in Biological Indicators Biological Indicators with different pH-value combinations of spore coating solution buffers and ampoule media were exposed to various lengths of $H_2O_2$ exposure time in sterilization vessel cycles averaging 6 mg/l $H_2O_2$ In a STERILUCENT PSD-85 hydrogen peroxide sterilizer. The impact of spore coating solution pH was investigated. After exposure to the hydrogen peroxide, the biological indicators were activated and then incubated in 490H Auto-readers. The Auto-readers were configured to record the amount of time it took to indicate positive fluorescence. The fluorescence readout result was compared with a visual observation (within up to 7 days of incubation) of pH color change in the growth media (purple to yellow in positive BIs). The representative time-to-turn fluorescence positive data or time to result (TTR) presented in Tables 6A-D are from biological indicators showing a visual color change from purple to yellow.

These comparison data showed the biological indicators with both ampoule media (Amp) pH and spore coating solution buffer (Sp) had the fastest time-to-turn fluorescence positive, with best consistency of readout and with less spreading and tailing as indicated by the lower standard deviations. Readout times for Amp-pH8/Sp-pH8 were less than 30 minutes and displayed the least amount of spreading and/or tailing.

TABLE 6A

Fluorescent time to results (TTR) data for ampoule media pH 7.5 and spore coating solution buffer pH 7 as function of exposure time (contact time between sterilant and biological indicator)

| Amp-pH7.5/ | Exposure time | | | |
|---|---|---|---|---|
| Sp-pH7 | 20 seconds | 47 seconds | 50 seconds | 52 seconds |
| Time to result (minutes) | 4 ± 0 | 9 ± 3 | 16 ± 11 | 21 ± 10 |

TABLE 6B

Fluorescent time to results (TTR) data for ampoule media pH 8 and spore coating solution buffer pH 7

| Amp-pH8/ | Exposure time | | | | |
|---|---|---|---|---|---|
| Sp-pH7 | 20 seconds | 45 seconds | 47 seconds | 52 seconds | 90 seconds |
| Time to result (minutes) | 4 ± 0 | 5 ± 2 | 10 ± 5 | 15 ± 6 | 52 ± 0* |

*Data obtained from only one positive out of twenty total biological indicators

TABLE 6C

Fluorescent time to results (TTR) data for ampoule media pH 7.5 and spore coating solution buffer pH 8

| Amp-pH7.5/ | Exposure time | | | | |
|---|---|---|---|---|---|
| Sp-pH8 | 20 seconds | 47 seconds | 50 seconds | 85 seconds | 90 seconds |
| Time to result (minutes) | 4 ± 0 | 6 ± 2 | 8 ± 2 | 8 ± 2 | 76 ± 88 |

TABLE 6D

Fluorescent time to results (TTR) data for ampoule media pH 8 and spore coating solution buffer pH 8

| Amp-pH8/ | Exposure time | | | |
|---|---|---|---|---|
| Sp-pH8 | 20 seconds | 47 seconds | 50 seconds | 52 seconds |
| Time to result (minutes) | 4 ± 0 | 7 ± 3 | 7 ± 2 | 9 ± 2 |

Example 6: Combined Effects of pH Adjustment of Spore Coatings and Liquid Medium on Fluorescent Detection of Surviving Spores in Biological Indicators This Example was conducted as described in Example 5 and the time to result (TTR) for each sterilization cycle condition was recorded by the auto-reader. In addition, for the biological indicators exposed to the sterilant during each exposure time, the biological indicators were visually observed for up to 7 days of incubation to determine whether the pH indicator had changed from purple to yellow. The pH color change from purple to yellow is considered to indicate growth of spores that survived exposure to the sterilization process. The results are shown in Tables 7A-7D.

TABLE 7A

Fluorescent and pH color change results data for ampoule media pH 7.5 and spore coating solution buffer pH 7. The results show the percentage of biological indicators exhibiting positive fluorescence or positive color change at each respective exposure duration.

| | Exposure time | | | | | |
|---|---|---|---|---|---|---|
| Amp-pH7.5/Sp-pH7 | 20 seconds | 47 seconds | 50 seconds | 52 seconds | 90 seconds | 240 seconds |
| Fluorescence positive | 100% | 100% | 100% | 100% | 95% | 0% |
| pH color change positive | 100% | 100% | 95% | 65% | 0% | 0% |

TABLE 7B

Fluorescent and pH color change results data for ampoule media pH 8 and spore coating solution buffer pH 7. The results show the percentage of biological indicators exhibiting positive fluorescence or positive color change at each respective exposure duration.

| | Exposure time | | | | | |
|---|---|---|---|---|---|---|
| Amp-pH8/Sp-pH7 | 20 seconds | 45 seconds | 47 seconds | 52 seconds | 90 seconds | 240 seconds |
| Fluorescence positive | 100% | 100% | 100% | 100% | 100% | 0% |
| pH color change positive | 100% | 100% | 95% | 70% | 5% | 0% |

TABLE 7C

Fluorescent and pH color change results data for ampoule media pH 7.5 and spore coating solution buffer pH 8. The results show the percentage of biological indicators exhibiting positive fluorescence or positive color change at each respective exposure duration.

| | Exposure time | | | | | |
|---|---|---|---|---|---|---|
| Amp-pH7.5/Sp-pH8 | 20 seconds | 47 seconds | 50 seconds | 85 seconds | 90 seconds | 240 seconds |
| Fluorescence positive | 100% | 100% | 100% | 40% | 55% | 0% |
| pH color change positive | 100% | 100% | 100% | 50% | 55% | 0% |

TABLE 7D

Fluorescent and pH color change results data for ampoule media pH 8 and spore coating solution buffer pH 8. The results show the percentage of biological indicators exhibiting positive fluorescence or positive color change at each respective exposure duration.

| | Exposure time | | | | | |
|---|---|---|---|---|---|---|
| Amp-pH8/Sp-pH8 | 20 seconds | 47 seconds | 50 seconds | 52 seconds | 90 seconds | 240 seconds |
| Fluorescence positive | 100% | 100% | 100% | 100% | 5% | 0% |
| pH color change positive | 100% | 100% | 100% | 70% | 0% | 0% |

The data show that the combination of Amp-pH8/Sp-pH8 provided the earliest detection (see Table 10D). Similar results were observed when the pH buffers were added directly to spore coating solution (See, for example, Tables 6C-6D).

Reference Example 2. D-Values of Biological Indicators Having Various Combinations of pH-Adjusted Spore Coatings and Nutrient Media Biological indicators with various combinations of pH-adjusted spore coatings and ampoulized media were prepared as described in Example 1. The biological indicators were exposed to $H_2O_2$ sterilization processes (in a PSD-85 $H_2O_2$ sterilizer) in order to calculate the D-value of the biological indicators. A commercially-available biological indicator (3M Part No. 1295; available from 3M Company, St. Paul, Minn.) was similarly tested for comparison. The results are shown in Table 8.

TABLE 8

D-values of BIs with pH combinations in $H_2O_2$ cycles

| | Amp-pH7.5/Sp-pH7 | Amp-pH8/Sp-pH7 | Amp-pH7.5/Sp-pH8 | Amp-pH8/Sp-pH8 | 3M 1295 Biological Indicator |
|---|---|---|---|---|---|
| D-Value | 9.0 seconds | 9.6 seconds | 16.2 seconds | 9.0 seconds | 5.5 seconds |

Example 7: Effect of Salt on Fluorescence Signal in Hydrogen Peroxide Biological Indicators The inventors have discovered that, in certain instances when a hydrogen peroxide sterilizer is overfilled with articles to be sterilized, it can result in some biological indicators exhibiting positive fluorescence even when it appeared all of the spores were killed (i.e., the growth medium remained purple after 7 days of incubation). However, the inventors have discovered that the inclusion of a salt in the biological indicator can reduce the incidence of fluorescence positive-growth negative results in biological indicators of the present disclosure.

Biological Indicators containing ampoule media formulation with 0.01M potassium phosphate were made as described in Example 1. In addition, some of the ampoulized medium was prepared using a lower concentration of MUG. The biological indicators were tested in a commercial $H_2O_2$ sterilizers STERRAD 100NX sterilizer and STERRAD 100S sterilizer that was overloaded with articles based on the recommended capacity for the sterilizers. After exposing the biological indicators to the sterilization process, they were activated and placed into a 490H Auto-reader to determine whether each biological indicator exhibited positive fluorescence. Data are presented in Table 9. The results showed the incidence of fluorescence positive-growth negative is reduced by adding salt to the biological indicator and by reducing the concentration of MUG in the nutrient medium (growth results not shown).

TABLE 9

Number of fluorescence positive biological indicator in customer overloaded cycles.

| | 100S cycle | 100NX cycle |
| --- | --- | --- |
| 225 mg/L MUG-0.01M salt | 0/12 | 0/12 |
| 300 mg/L MUG-0.01M salt | 3/12 | 0/12 |
| 3M 1295 Biological Indicator (Control) | 6/24 | 0/18 |

Example 8: Effect of Nutrient Medium pH Impact on the Detection of Spore Survival After Exposure to an $H_2O_2$ Sterilization Process Biological Indicators for steam sterilization processes were prepared as described in Example 1. The ampoules of nutrient medium were removed after the sterilization process and the nutrient medium indicated in Table 14 was aseptically pipetted into each biological indicator. The indicators were exposed to sub-lethal 132.2° C. vacuum-assisted cycles in a (H & W Technology) steam resistometer vessel. Nutrient media adjusted to different pH values were added to the exposed biological indicators and the biological indicators were activated by pipetting the nutrient medium into the biological indicators prior to incubation in 490 Auto-readers. The auto-readers were configured to record the time at which a positive fluorescent signal was detected in each biological indicator. Representative time-to-turn fluorescence positive data are presented in Table 10. Seven-day visual readout.

TABLE 10

Ampoule media pH effects on BI performance after exposure to a 132.2° C. vacuum-assisted steam sterilization cycle

| Media pH | Fluorescence Result (#positive/# tested) | pH Color Change Result (#yellow media/#tested) | Visual Color Change Result | Time to Result (Minutes) |
| --- | --- | --- | --- | --- |
| 7.50 | 5/5 | 5/5 | Bright yellow | 19 ± 3 |
| 7.81 | 5/5 | 5/5 | Bright yellow | 18 ± 2 |
| 7.98 | 5/5 | 5/5 | Bright yellow | 17 ± 1 |
| 8.04 | 5/5 | 5/5 | Bright yellow | 16 ± 2 |
| 8.19 | 5/5 | 5/5 | Bright yellow | 12 ± 3 |
| 8.40 | 5/5 | 5/5 | Bright yellow | 13 ± 3 |
| 8.62 | 5/5 | 5/5 | Yellow | 15 ± 1 |
| 9.03 | 5/5 | 5/5 | Darker yellow | 20 ± 7 |

Example 9: Testing in Different Steam Sterilization Cycles

These experiments were performed as described in Example 8 except the exposure to steam was performed at the indicated temperatures in dynamic air removal sterilization processes. Time to result data were generated using various steam sterilization cycle temperatures, conditions and parameters. Table 11 shows representative data comparing BIs with ampoule media of pH 7.5 to biological indicators with ampoule media of pH 8.0 in two different steam sterilization cycles (121° C. and 132° C., respectively).

TABLE 11

Ampoule media pH effect on biological indicator time to results after exposure to 121° C. and 132° C. dynamic air removal steam sterilization cycles.

| | 121° C. | 132° C. |
| --- | --- | --- |
| Ampoule media at pH 7.5 Time to results (minutes) | 49 ± 8 | 39 ± 18 |
| Ampoule media at pH 8.0 Time to results (minutes) | 27 ± 13 | 20 ± 3 |

The relative time to results in both cases were lower in the BIs with ampoule media of pH 8.0.

Example 10: Combined Effects of pH Adjustment of Spore Coatings and Liquid Medium on Fluorescent Detection of Surviving Spores in Biological Indicators Biological Indicators for steam sterilization processes, with various pH-value combinations of spore coating solution buffers and ampoule media, were exposed to different steam cycle times were prepared as described in Example 1. Data were generated by exposing biological indicators to sub-lethal 132.2° C. vacuum-assisted cycles in a (H&W Technology) steam resistometer vessel. Exposed biological indicators were processed and incubated in 490 Auto-readers that were configured to record the time at which positive fluorescence was detected in each biological indicator. The fluorescence readout result was compared with a visual observation of pH color change in the growth media. The time-to-turn fluorescence positive data presented in Table 12 are only from biological indicators showing a visual color change from purple to yellow.

TABLE 12

Time to results data for ampoule media and spore coating solution buffer pH combinations

|  | Amp-pH7.5/ Sp-pH7 | Amp-pH8/ Sp-pH7 | Amp-pH7.5/ Sp-pH8 | Amp-pH8/ Sp-pH8 |
|---|---|---|---|---|
| Time to result (minutes) | 30 ± 4 | 24 ± 9 | 25 ± 11 | 18 ± 5 |

These data showed the biological indicators with both spore coating solution buffer and ampoule media adjusted to pH 8 (Amp-pH8/Sp-pH8) had the fastest time-to-turn fluorescence positive readouts with less spreading or tailing of data.

Example 11: Comparison of the Fluorescence Readout and pH Color Change

Biological indicators for steam sterilization processes were prepared as described in Example 10. The indicators were exposed to steam sterilization processes of various lengths of time (as indicated) at 312.2 degrees in a vacuum-assisted sterilization process in a (H & W Technology) steam resistometer. After exposure to the steam sterilization processes, the biological indicators were activated and placed into a 490 Auto-reader that was configured to detect positive fluorescence within 60 minutes of incubation. In addition, after incubation, the color of the nutrient medium was visually observed (7 days) to detect whether the color of the pH indicator changed from purple to yellow.

TABLE 133A

Fluorescent and pH color change results data for ampoule media pH 7.5 and spore coating solution buffer pH 8

| Amp-pH7.5/ Sp-pH7 | Exposure time | | | | |
|---|---|---|---|---|---|
| | 120 seconds | 150 seconds | 160 seconds | 180 seconds | 240 seconds |
| Fluorescence positive | 100% | 100% | 37% | 0% | 0% |
| pH color change positive | 100% | 87% | 0% | 0% | 0% |

TABLE 13B

Fluorescent and pH color change results data for ampoule media pH 7.5 and spore coating solution buffer pH 8

| Amp-pH8/ Sp-pH7 | Exposure time | | | | |
|---|---|---|---|---|---|
| | 120 seconds | 180 seconds | 185 seconds | 195 seconds | 200 seconds |
| Fluorescence positive | 100% | 60% | 43% | 12% | 0% |
| pH color change positive | 100% | 60% | 0% | 12% | 0% |

TABLE 13C

Fluorescent and pH color change results data for ampoule media pH 7.5 and spore coating solution buffer pH 8

| Amp-pH7.5/ Sp-pH8 | Exposure time | | | | |
|---|---|---|---|---|---|
| | 120 seconds | 150 seconds | 160 seconds | 180 seconds | 240 seconds |
| Fluorescence positive | 100% | 100% | 87% | 0% | 0% |
| pH color change positive | 100% | 100% | 37% | 0% | 0% |

TABLE 13D

Fluorescent and pH color change results data for ampoule media pH 8 and spore coating solution buffer pH 8

| Amp-pH8/ Sp-pH8 | Exposure time | | | | |
|---|---|---|---|---|---|
| | 120 seconds | 150 seconds | 160 seconds | 180 seconds | 240 seconds |
| Fluorescence positive | 100% | 100% | 62% | 0% | 0% |
| pH color change positive | 100% | 100% | 37% | 0% | 0% |

Example 12: Application to Steam Biological Indicator

Figure 3:
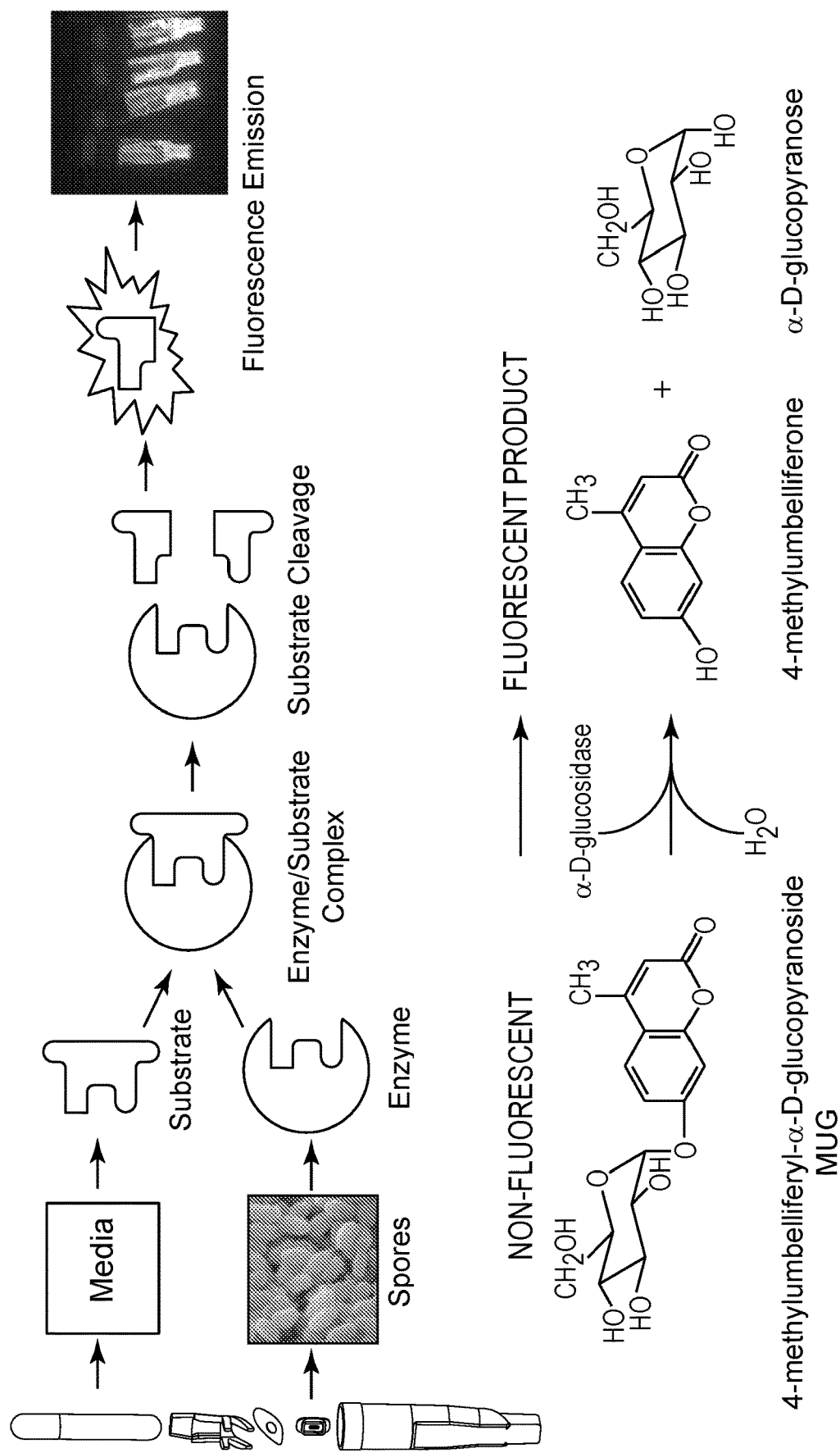
FIG. 3 is an exemplary description of a rapid readout chemistry

Potassium phosphate was added to the ampoule media at different concentrations and the biological indicator performance was tested. Results are presented in FIG. 3. Here we showed that when potassium phosphate is added to 1295 ampoule media and tested in $H_2O_2$ cycles, the growth response is impacted, whereas the fluorescence sign remained the same. The same conclusion is observed in steam sterilization (FIG. 4).

Example 13: Application to Universal Biological Indicator

Biological indicators for steam sterilization processes were prepared according to Example 1 with the ampoule media adjusted to pH 8. The indicators were exposed to steam in various gravity and dynamic air removal steam sterilization cycles in a (H & W Technology) steam resistometer. After exposure to the steam processes, the biological indicators were activated and were placed into a 490 Auto-reader that was configured to detect positive fluorescence within 24 minutes of incubation. Data showing the percent fluorescence positive and percent growth positive are presented in Table 14A-K. In each sterilization process, the shortest exposure time (i.e., "survival cycle") resulted in the survival of at least one spore in every BI tested and the longest exposure time (i.e., "kill cycle") resulted in the killing of every spore in every BI tested. Intermediate exposure times, with less than 100% survival and less than 100% kill were considered "fractional cycles".

TABLE 14A 121.1° C. Gravity steam sterilization cycle

| Exposure Time | % Fl. Pos. | Growth Pos. |
|---|---|---|
| 12:10 | 100% | 84% |
| 12:30 | 92% | 68% |
| 12:38 | 100% | 52% |
| 14:00 | 24% | 0% |
| 15:00 | 0% | 0% |
| 17:00 | 0% | 0% |

TABLE 14B 121.1° C. Pre-vacuum steam sterilization cycle

| Exposure Time | % Fl. Pos. | Growth Pos. |
|---|---|---|
| 10:00 | 100% | 100% |
| 10:22 | 98% | 75% |
| 10:25 | 92% | 36% |
| 10:45 | 32% | 16% |
| 12:00 | 4% | 0% |
| 14:00 | 0% | 0% |
| 17:00 | 0% | 0% |

TABLE 14C 121.1° C. SFPP steam sterilization cycle

| Exposure Time | % Fl. Pos. | Growth Pos. |
|---|---|---|
| 12:00 | 100% | 100% |
| 12:55 | 100% | 38% |
| 13:30 | 98% | 38% |
| 18:00 | 32% | 8% |
| 21:59 | 0% | 0% |
| 22:13 | 0% | 0% |

TABLE 14D 132.2° C. Gravity steam sterilization cycle

| Exposure Time | % Fl. Pos. | Growth Pos. |
|---|---|---|
| 3:30 | 100% | 100% |
| 3:45 | 100% | 76% |
| 3:48 | 100% | 78% |
| 4:00 | 100% | 9% |
| 4:15 | 100% | 2% |
| 5:30 | 10% | 0 |
| 6:00 | 0% | 0 |

TABLE 14E 132.2° C. Pre-vacuum steam sterilization cycle

| Exposure Time | % Fl. Pos. | Growth Pos. |
|---|---|---|
| 3:20 | 100% | 100% |
| 3:30 | 100% | 56% |

TABLE 14E-continued 132.2° C. Pre-vacuum steam sterilization cycle

| Exposure Time | % Fl. Pos. | Growth Pos. |
|---|---|---|
| 3:38 | 100% | 56% |
| 3:50 | 100% | 20% |
| 4:10 | 100% | 0% |
| 4:50 | 72% | 0% |
| 5:20 | 4% | 0% |
| 5:28 | 0% | 0% |
| 5:50 | 0.0% | 0% |

TABLE 14F 132.2° C. SFPP steam sterilization cycle

| Exposure Time | % Fl. Pos. | Growth Pos. |
|---|---|---|
| 3:00 | 100% | 100% |
| 3:20 | 100% | 48% |
| 3:48 | 100% | 70% |
| 4:25 | 100% | 4% |
| 4:55 | 92% | 0% |
| 5:20 | 4% | 0% |
| 6:01 | 0% | 0% |

TABLE 14G 134.0° C. Pre-vacuum steam sterilization cycle

| Exposure Time | % Fl. Pos. | Growth Pos. |
|---|---|---|
| 3:10 | 100% | 100% |
| 3:25 | 100% | 78% |
| 3:30 | 100% | 74% |
| 4:00 | 84% | 6% |
| 4:10 | 72% | 0% |
| 4:40 | 12% | 0% |
| 4:50 | 0% | 0% |
| 5:10 | 0% | 0% |

TABLE 14H 134.0° C. SFPP steam sterilization cycle

| Exposure Time | % Fl. Pos. | Growth Pos. |
|---|---|---|
| 3:00 | 100% | 100% |
| 3:25 | 100% | 54% |
| 3:35 | 100% | 37% |
| 3:45 | 84% | 0% |
| 5:00 | 0% | 0% |
| 5:28 | 0% | 0% |

TABLE 14I 135.0° C. Gravity steam sterilization cycle

| Exposure Time | % Fl. Pos. | Growth Pos. |
|---|---|---|
| 2:45 | 100% | 100% |
| 3:10 | 100% | 48% |
| 3:15 | 100% | 42% |
| 4:00 | 84% | 0% |

TABLE 14I-continued 135.0° C. Gravity steam sterilization cycle

| Exposure Time | % Fl. Pos. | Growth Pos. |
|---|---|---|
| 4:45 | 0% | 0% |
| 5:08 | 0% | 0% |

TABLE 14J 135.0° C. Pre-vacuum steam sterilization cycle

| Exposure Time | % Fl. Pos. | Growth Pos. |
|---|---|---|
| 3:00 | 100% | 100% |
| 3:10 | 100% | 52% |
| 3:15 | 100% | 48% |
| 4:35 | 4% | 0% |
| 4:50 | 0% | 0% |

TABLE 14K 135.0° C. SFPP steam sterilization cycle

| Exposure Time | % Fl. Pos. | Growth Pos. |
|---|---|---|
| 3:00 | 100% | 100% |
| 3:25 | 100% | 40% |
| 3:35 | 100% | 36% |
| 3:45 | 90% | 18% |
| 4:30 | 8% | 0% |
| 4:55 | 0% | 0% |
| 5:00 | 0% | 0% |

Example 14: Application to Universal Test Pack

Biological indicators for steam sterilization processes were prepared according to Example 1 with the ampoule media adjusted to pH 8. The indicators were placed into Challenge Packs (3M™ Attest™ Super Rapid 5 Steam-Plus Challenge Pack; Part No. 41482V; obtained from 3M Company, St. Paul, Minn.) or 16-Towel packs (prepared according to ANSI/AAMI ST79:2017), which were then exposed to steam in various gravity and dynamic air removal steam sterilization cycles in AMSCO 3013C sterilizers. After exposure to the steam processes, the biological indicators were activated and were placed into a 490 Auto-reader that was configured to detect positive fluorescence within 24 minutes of incubation. In addition, after incubation, the color of the nutrient medium was visually observed for up to 7 days to detect whether the color of the pH indicator changed from purple to yellow. Data are presented in Table 15A-E. Each table demonstrates biological indicator performance in each of the respective cycle types.

TABLE 15A 121.1° C. Gravity Test Pack steam sterilization cycle

| Cycle type | Test Pack configuration | % Fl. Pos. | Growth Pos. |
|---|---|---|---|
| Survival cycle | Challenge Pack | 100% | 100% |
|  | 16 Towel Packs | 100% | 100% |
| Fractional cycle | Challenge Pack | 75% | 25% |
|  | 16 Towel Packs | 58% | 25% |
| Half cycle | Challenge Pack | 100% | 100% |
|  | 16 Towel Packs | 100% | 92% |
| Kill cycle | Challenge Pack | 0% | 0% |
|  | 16 Towel Packs | 0% | 0% |

TABLE 15B 121.1° C. Pre-vacuum Test Pack steam sterilization cycle

| Cycle type | Test Pack configuration | % Fl. Pos. | Growth Pos. |
|---|---|---|---|
| Survival cycle | Challenge Pack | 100% | 100% |
|  | 16 Towel Packs | 100% | 100% |
| Fractional cycle | Challenge Pack | 42% | 25% |
|  | 16 Towel Packs | 42% | 17% |
| Half cycle | Challenge Pack | 0% | 0% |
|  | 16 Towel Packs | 0% | 0% |
| Kill cycle | Challenge Pack | 0% | 0% |
|  | 16 Towel Packs | 0% | 0% |

TABLE 15C 132.2° C. Gravity Test Pack steam sterilization cycle

| Cycle type | Test Pack configuration | % Fl. Pos. | Growth Pos. |
|---|---|---|---|
| Survival cycle | Challenge Pack | 100% | 100% |
|  | 16 Towel Packs | 100% | 100% |
| Fractional cycle | Challenge Pack | 83% | 67% |
|  | 16 Towel Packs | 83% | 58% |
| Half cycle | Challenge Pack | 100% | 100% |
|  | 16 Towel Packs | 100% | 100% |
| Kill cycle | Challenge Pack | 0% | 0% |
|  | 16 Towel Packs | 0% | 0% |

TABLE 15C 132.2° C. Pre-vacuum Test Pack steam sterilization cycle

| Cycle type | Test Pack configuration | % Fl. Pos. | Growth Pos. |
|---|---|---|---|
| Survival cycle | Challenge Pack | 100% | 100% |
|  | 16 Towel Packs | 100% | 100% |
| Fractional cycle | Challenge Pack | 100% | 92% |
|  | 16 Towel Packs | 92% | 83% |
| Half cycle | Challenge Pack | 0% | 0% |
|  | 16 Towel Packs | 0% | 0% |
| Kill cycle | Challenge Pack | 0% | 0% |
|  | 16 Towel Packs | 0% | 0% |

TABLE 15D 134.0° C. Pre-vacuum Test Pack steam sterilization cycle

| Cycle type | Test Pack configuration | % Fl. Pos. | Growth Pos. |
|---|---|---|---|
| Survival cycle | Challenge Pack | 100% | 100% |
|  | 16 Towel Packs | 100% | 100% |
| Fractional cycle | Challenge Pack | 92% | 92% |
|  | 16 Towel Packs | 92% | 83% |
| Half cycle | Challenge Pack | 0% | 0% |
|  | 16 Towel Packs | 0% | 0% |

TABLE 15D-continued 134.0° C. Pre-vacuum Test Pack steam sterilization cycle

| Cycle type | Test Pack configuration | % Fl. Pos. | Growth Pos. |
|---|---|---|---|
| Kill cycle | Challenge Pack | 0% | 0% |
| | 16 Towel Packs | 0% | 0% |

TABLE 15E 135.0° C. Pre-vacuum Test Pack steam sterilization cycle

| Cycle type | Test Pack configuration | % Fl. Pos. | Growth Pos. |
|---|---|---|---|
| Survival cycle | Challenge Pack | 100% | 100% |
| | 16 Towel Packs | 100% | 100% |
| Fractional cycle | Challenge Pack | 100% | 100% |
| | 16 Towel Packs | 33% | 17% |
| Half cycle | Challenge Pack | 100% | 75% |
| | 16 Towel Packs | 25% | 17% |
| Kill cycle | Challenge Pack | 0% | 0% |
| | 16 Towel Packs | 0% | 0% |

We claim:

1. A self-contained biological indicator comprising:
a housing;
a source of biological activity, the source comprising and/or capable of producing an enzyme capable of catalyzing a cleavage of an enzyme substrate; and
an actuatable container comprising a liquid composition, comprising the enzyme substrate, wherein the enzyme substrate comprises a fluorophore component that, when separated from the enzyme substrate by the enzyme, comprises 7-hydroxy-2H-chromen-2-one or a derivative thereof;
wherein the actuatable container can be actuated to allow the liquid composition to contact a bacterial spore; and
wherein the source of biological activity and/or the liquid composition comprises an effective amount of an acidic component and/or a basic component such that, when the source of biological activity and the liquid composition are combined, a resulting mixture of the source of biological activity and the liquid composition has an initial pH greater than or equal to a pKa of a hydroxyl group of the fluorophore component.

2. The self-contained biological indicator of claim 1, wherein the fluorophore component is selected from the group consisting of 4-methyl-5-fluoro-2H-chromen-2-one, 4-methyl-6-fluoro-2H-chromen-2-one, 4-methyl-8-fluoro-2H-chromen-2-one, 4-methyl-6,8-difluoro-2H-chromen-2-one, 4-methyl-6-chloro-2H-chromen-2-one, and 4-methyl-ethanoate-6-fluoro-2H-chromen-2-one.

3. The self-contained biological indicator of claim 1, wherein the enzyme is selected from the group consisting of α-glucosidase, α-galactosidase, lipase, esterase, acid phosphatase, alkaline phosphatase, proteases, aminopeptidase, chymotrypsin, β-glucosidase, β-galactosidase, α-glucoronidase, β-glucoronidase, phosphohydrolase, plasmin, thrombin, trypsin, calpain, α-mannosidase, β-mannosidase, a-L-fucosidase, leucine aminopeptidase, a-L-arabinofuranosidase, cysteine aminopeptidase, valine aminopeptidase, β-xylosidase, α-L-iduronidase, glucanase, cellobiosidase, cellulase, α-arabinosidase, glycanase, sulfatase, butyrate, glycosidase, arabinosidase, and a combination thereof.

4. The self-contained biological indicator of claim 1, wherein the enzyme substrate comprises a derivative of 4-methylumbelliferone or a derivative of 7-amino-4-methylcoumarin.

5. The self-contained biological indicator of claim 1, wherein the enzyme comprises α-D-glucosidase, wherein the enzyme substrate comprises 4-methylumbelliferyl-α-D-glucopyranoside.

6. A system, comprising
the self-contained biological indicator of claim 1; and
an automated reader configured to:
receive at least a portion of the self-contained biological indicator;
direct a first wavelength of electromagnetic radiation into the liquid composition in the housing; and
detect or measure a quantity of a second wavelength of electromagnetic radiation emitted by a fluorescent product.

7. The system of claim 6, wherein the self-contained biological indicator is adapted to be used to determine efficacy of any steam sterilization process selected from the group consisting of 121° C. gravity process, 121° C. pre-vac process, 121° C. SFPP process, 132° C. gravity process, 132° C. pre-vac process, 132° C. SFPP process, 134° C. pre-vac process, 134° C. SFPP process, 135° C. gravity process, 135° C. pre-vac process, and 135° C. SFPP process.

* * * * *